US008288548B2

(12) United States Patent
Coates et al.

(10) Patent No.: US 8,288,548 B2
(45) Date of Patent: Oct. 16, 2012

(54) OXAZOLO[5-4-B]PYRIDIN-5-YL COMPOUNDS

(75) Inventors: David Andrew Coates, Indianapolis, IN (US); Raymond Gilmour, Indianapolis, IN (US); Jose Alfredo Martin, Madrid (ES); Eva Maria Martin de la Nava, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/298,319

(22) Filed: Nov. 17, 2011

(65) Prior Publication Data

US 2012/0142724 A1 Jun. 7, 2012

Related U.S. Application Data

(60) Provisional application No. 61/439,151, filed on Feb. 3, 2011.

(30) Foreign Application Priority Data

Dec. 3, 2010 (EP) ..................................... 10382329

(51) Int. Cl.
C07D 471/02 (2006.01)
A61K 31/44 (2006.01)
(52) U.S. Cl. ........................................ 546/115; 514/302
(58) Field of Classification Search .................. 546/115; 514/302
See application file for complete search history.

(56) References Cited

FOREIGN PATENT DOCUMENTS

| WO | 01/62756 A1 | 8/2001 |
|---|---|---|
| WO | 2004/014900 A1 | 2/2004 |
| WO | 2005075478 | 8/2005 |
| WO | 2005120509 | 12/2005 |
| WO | 2007016392 | 2/2007 |
| WO | 2009017822 | 2/2009 |

OTHER PUBLICATIONS

Zips et. al., "New Anticancer Agents: In Vitro and In Vivo Evaluation", In Vivo 19:1-8 (2005).*

* cited by examiner

*Primary Examiner* — Nizal Chandrakumar
(74) *Attorney, Agent, or Firm* — Tina M. Tucker

(57) ABSTRACT

The present invention provides oxazolo[5,4-b]pyridin-5-yl compounds useful in the treatment of cancer.

13 Claims, No Drawings

OXAZOLO[5-4-B]PYRIDIN-5-YL COMPOUNDS

This application claims the benefit of U.S. Provisional Application No. 61/439,151, filed Feb. 3, 2011 and European Provisional Application No. 10382329.0 filed 3 Dec. 2010.

The p38 MAP kinase is a mitogen-activated protein (MAP) kinase that belongs to the serine/threonine kinase superfamily. This kinase is activated by extracellular stresses such as heat, UV light, and osmotic stress, as well as by inflammatory stimuli such as lipopolysaccharides. When activated, p38 MAP kinase phosphorylates intracellular protein substrates that regulate the biosynthesis of the pro-inflammatory cytokines tumor necrosis factor α (TNFα), interleukin-1β (IL-1β), interleukin 6 (IL-6) and interleukin 8 (IL-8). These cytokines are implicated in the pathology of a number of chronic inflammatory disorders. Chronic inflammation is a key risk factor for cancer development. For example, the p38 MAP kinase pathway is a target of the Kaposi's Sarcoma associated Herpes Virus (KSHV) which results in chronic inflammation and development of sarcoma. In addition, the cytokines regulated by p38 MAP kinase, such as IL-8, have been implicated in driving angiogenesis associated with tumor growth. The phosphorylated form of mitogen-activated protein kinase-protein kinase 2 (or pMAPKAPK2) is also a kinase in the p38 MAP kinase pathway and can be directly activated by p38 MAP kinase. Mouse knockout studies of MAPKAPK2 show a reduction in cytokine production suggesting MAPKAPK2 can be a key regulator of the inflammatory response and can also be a potential target for anti-inflammatory and/or cancer therapy (WO2005120509).

Azabenzothiazolyl p38 MAP kinase inhibitors (for example, WO2007016392) have been disclosed in the art for the treatment of anti-inflammatory diseases. Additionally, azabenzimidazolyl p38 MAP kinase inhibitors (for example, WO2005075478) have been disclosed in the art for the treatment of cancer. Further, WO200917822 discloses imidazolyl oxazoles and oxazolo[4,5-b]pyridine-6-yls useful as inhibitors of PI3 kinase.

However, certain p38 MAP kinase inhibitors or cytokine inhibitors may have bioavailability and absorption problems that limit their in vivo effects and therapeutic use. Additionally, certain p38 MAP kinase inhibitors may present adverse toxicological effects (especially GI toxicity) to a patient and harbor risks of patient drug-drug interactions. Therefore, a need exists for alternative cytokine suppressive drugs. Preferably such compounds are capable of inhibiting p38 MAP kinase with improved potency and greater bioavailability. Preferably such compounds also have an improved toxicology profile (especially GI toxicity) and decreased risk of patient drug-drug interactions.

The present invention provides novel oxazolo[5,4-b]pyridin-5-yl compounds that may have clinical use as a single agent for treatment of cancer and particularly ovarian cancer and/or multiple myeloma. Further, the present invention provides novel oxazolo[5,4-b]pyridin-5-yl compounds that may have clinical use in combination with another therapeutic agent such as sunitinib for treatment of cancer and particularly renal cancer. Additionally, compounds of the present invention are potent p38 MAP kinase inhibitors (p38α, p38β, and p38 MAP kinase signaling in cancer cells) and may have an improved toxicology profile (especially GI toxicity) and decreased risk of patient drug-drug interactions compared to certain previously known p38 MAP kinase inhibitors.

The present invention provides compounds of Formula I:

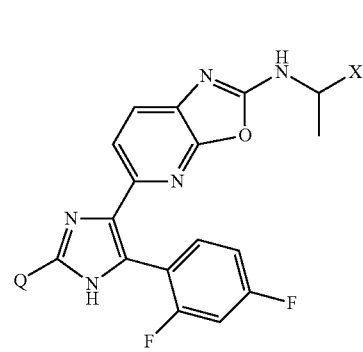

Formula I where:
X is methoxyethyl or ethoxymethyl;
Q is cyclopropyl, 2-methyl-propanol-2-yl, 3-methyloxetan-3-yl, 1-hydroxymethyl-1-cyclopropyl;
or a pharmaceutically acceptable salt thereof.

The present invention also provides crystalline 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol characterized by the X-ray powder diffraction pattern (Cu radiation, λ=1.54060 Å) comprising a peak at 15.06, and one or more peaks at 19.94, 10.31, and 20.78 (2θ+/−0.2°).

The present invention also provides crystalline 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol characterized by the X-ray powder diffraction pattern (Cu radiation, λ=1.54060 Å) comprising a peak at 13.73, and one or more peaks at 16.54, 22.87, and 18.57 (2θ+/−0.2°).

The present invention provides a compound which is 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol, or a pharmaceutically acceptable salt thereof.

The present invention provides a compound which is 5-[2-cyclopropyl-5-(2,4-difluorophenyl)-1H-imidazol-4-yl]-N-[(1S)-3-methoxy-1-methyl-propyl]oxazolo[5,4-b]pyridin-2-amine, or a pharmaceutically acceptable salt thereof.

The present invention provides a compound which is 5-[5-(2,4-difluorophenyl)-2-(3-methyloxetan-3-yl)-1H-imidazol-4-yl]-N-[(1S)-3-methoxy-1-methyl-propyl]oxazolo[5,4-b]pyridin-2-amine, or a pharmaceutically acceptable salt thereof.

The present invention provides a compound which is [1-[5-(2,4-difluorophenyl)-4-[2-[[(1S)-2-ethoxy-1-methylethyl]amino]oxazolo[5,4-b]pyridin-5-yl]-1H-imidazol-2-yl]cyclopropyl]methanol, or a pharmaceutically acceptable salt thereof.

The present invention provides a method of treating ovarian cancer in a mammal comprising administering to a mammal in need of such treatment an effective amount of a compound or salt of the present invention.

The present invention provides a method of treating multiple myeloma in a mammal comprising administering to a mammal in need of such treatment an effective amount of a compound or salt of the present invention.

The present invention provides a method of treating cancer, in particularly renal cancer, in a mammal comprising administering to a mammal in need of such treatment an effective amount of a compound or salt of the present invention in simultaneous, separate or sequential combination with sunitinib.

This invention also provides pharmaceutical compositions comprising a compound or salt of the present invention in combination with one or more pharmaceutically acceptable carriers, diluents, or excipients. In a particular embodiment the composition further comprises one or more other therapeutic agents. More particularly, the other therapeutic agent is sunitinib.

This invention also provides a compound or salt of the present invention for use in therapy. The invention also provides a compound or salt of the present invention for use in the treatment of cancer. Additionally, this invention provides use of a compound or salt of the present invention in the manufacture of a medicament for treating cancer. Additionally, this invention provides for use of a compound or salt of the present invention for use in the treatment of cancer. In particular this cancer is ovarian cancer. Additionally, this cancer is multiple myeloma.

This invention also provides a compound of the present invention, or a pharmaceutically acceptable salt thereof, and sunitinib as a combined preparation for simultaneous, separate or sequential use in therapy.

The invention also provides sunitinib for use in simultaneous, separate or sequential combination with a compound of the present invention, or pharmaceutically acceptable salt thereof, in the treatment of cancer. In the alternative the invention provides a compound of the present invention, or pharmaceutically acceptable salt thereof, for use in simultaneous, separate or sequential combination with sunitinib in the treatment of cancer. More particularly, the cancer is renal cancer.

It will be understood by the skilled reader that compounds of Formula I are capable of forming salts. The compounds of the present invention contain basic heterocycles, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

The skilled artisan will appreciate that compounds of the present invention contain at least one chiral center. The present invention contemplates all individual enantiomers or diastereomers, as well as mixtures of the enantiomers and diastereomers of said compounds including racemates. It is preferred that compounds of the present invention containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

Sunitinib, marketed as SUTENT®, is an oral, small-molecule, multi-targeted receptor tyrosine kinase inhibitor that was approved by the FDA for the treatment of renal cell carcinoma and imatinib-resistant gastrointestinal stromal tumors. Sunitinib is disclosed in WO200160814.

Scheme I
Preparation of compounds of Formula I, wherein R is cyclopropyl or 3-methyloxetan-3-yl; X is defined above.

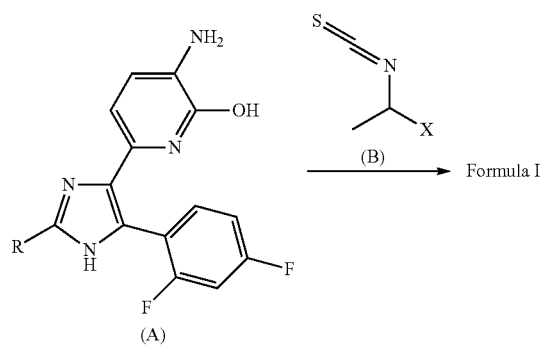

Ortho-hydroxypyridyl-3-amines (A) are treated with isothiocyanates (B), which may be racemic or a single enantiomer, in ethanol with heating. During heating and periodically, excess of an N,N'-disubstituted-carbodiimide is added to remove hydrogen sulfide. For example, N,N'-dicyclohexyl-carbodiimide, N,N'-diisopropyl-carbodiimide, or 1-ethyl-3-(3-dimethylaminopropyl)carbodiimide hydrochloride may be used. The synthesis of isothiocyanates (B), which may be racemic or a single enantiomer, are described in the preparations below.

Scheme II
Preparation of compounds of Formula I, wherein R is methyl 2-methyl-propanecarboxylate-2-yl or methyl cyclopropane carboxylate-1-yl; X is defined above.

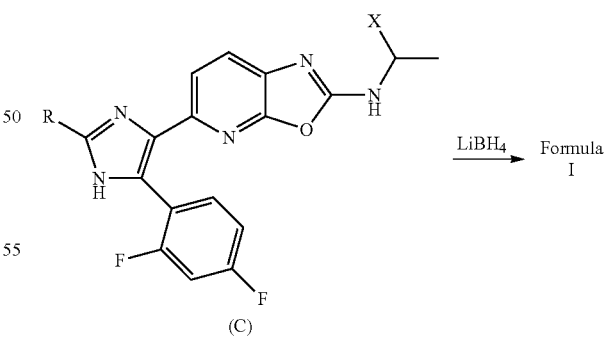

5-(1H-imidazol-4-yl)oxazolo[5,4-b]pyridines (C) are reduced with lithium borohydride in ether to give compounds of Formula I. The intermediates (C) are similarly prepared from the corresponding hydroxypyridyl-3-amines (A) (Scheme I), wherein R is methyl 2-methyl-propanecarboxylate-2-yl or methyl cyclopropane carboxylate-1-yl with isothiocyanates (B), as in Scheme I.

Scheme III
Synthesis of intermediates (A), wherein R is methyl 2-methyl-propanecarboxyate-2-yl, methyl cyclopropane carboxylate-1-yl, cyclopropyl, or 3-methyloxetan-3-yl

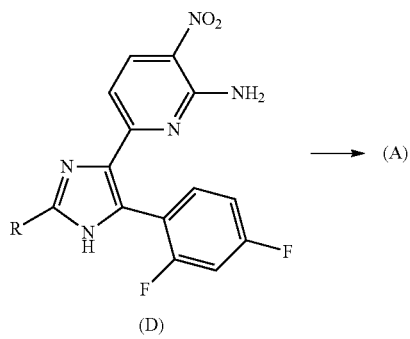

→ (A)

6-(1H-Imidazol-4-yl)-3-nitro-pyridin-2-amine (D) undergoes functional group manipulations on the pyridine ring involving diazotization of the 2-pyridyl amine group followed by water quench, then hydrogenation of the 3-pyridyl nitro group to give intermediates (A).

Scheme IV
Synthesis of intermediates (D), wherein R is as defined in Scheme III.

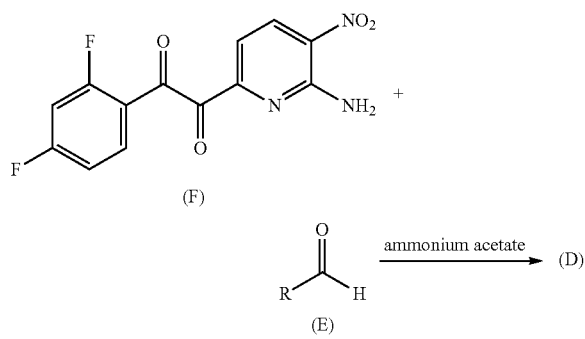

Intermediates (D) are prepared from 1-(6-amino-5-nitro-2-pyridyl)-2-(2,4-difluorophenyl)ethane-1,2-dione (F) and the known aldehydes (E) by heating in dioxane with ammonium acetate. The synthesis of intermediate (F) is described in the preparations below.

The compounds of the present invention are prepared essentially as illustrated in the Schemes, Preparations and Examples below. The reagents and starting materials are readily available to one of ordinary skill in the art or may be made by procedures which are selected from standard techniques of organic and heterocyclic chemistry, techniques which are analogous to the syntheses of known structurally similar compounds, and the procedures described in the Examples below, including any novel procedures. It should be understood that the Preparations and Examples are set forth by way of illustration and not limitation, and that various modifications may be made by one of ordinary skill in the art.

The naming of the following Preparations and Examples is generally done using the IUPAC naming feature in SYMYX® Draw version 3.2.NET.

PREPARATION 1 tert-Butyl (3S)-3-[benzyl-[(1S)-1-phenylethyl]amino]butanoate

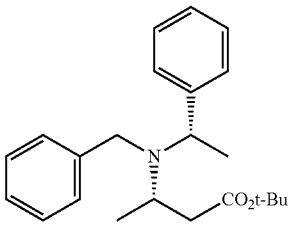

Preparations 1 and 2 have been described in WO 2006/076595 for the R,R enantiomer. See also Davies, S. G. and Ichihara, O. *Tetrahedron: Asymmetry* 1991, 2, 183-186 for asymmetric synthesis of 3-aminobutanoates from (E)-but-2-enoates (crotonates).

(1S)—N-Benzyl-1-phenyl-ethanamine (28.53 g, 135 mmol), is dissolved in anhydrous tetrahydrofuran (THF) and the solution is cooled to 0° C. under an argon atmosphere. N-Butyllithium (2.5 M in hexanes, 54 mL, 135 mmol) is added dropwise over 30 min. The reaction mixture is stirred for 20 min at 0° C. and then cooled to −78° C. A solution of tert-butyl (E)-but-2-enoate (10 g, 70.32 mmol) in anhydrous THF (75 mL) is added to the reaction mixture over 20 min. After 75 min, the reaction is quenched by adding a saturated solution of $NH_4Cl$ (175 mL) and saturated aqueous NaCl (brine, 100 mL). The layers are separated and the aqueous layer is extracted with diethyl ether (2×125 mL). The combined organic layers are dried over anhydrous $MgSO_4$, filtered, and concentrated to afford a yellow oil. The crude product is dissolved in hexanes (250 mL) and washed with a 10% aqueous citric acid solution (3×75 mL). The organic layer is dried over $MgSO_4$, filtered, and concentrated to afford the title compound as a yellow oil (24.12 g, 97%). LC-ES/MS m/z 354 (M+1).

PREPARATION 2

(3S)-3-[Benzyl-[(1S)-1-phenylethyl]amino]butan-1-ol

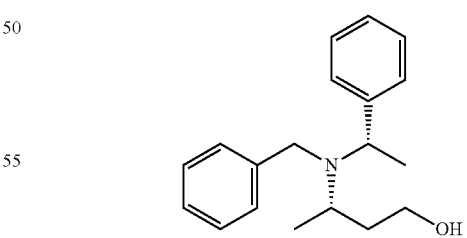

tert-Butyl (3S)-3-[benzyl-[(1S)-1-phenylethyl]amino]butanoate (24 g, 67.9 mmol) is dissolved in anhydrous THF (237 mL) and cooled to 0° C. under an argon atmosphere. 1 M Lithium aluminum hydride in THF (237 mL, 237 mmol) is added dropwise over 10 min. The reaction mixture is stirred at 0° C. for 1 h and then at 60° C. for 1 h. The mixture is cooled to room temperature (RT) and diluted with diethyl ether (500 mL). The reaction is quenched with a mixture of CELITE® and Na$_2$SO$_4$.10 H$_2$O (1:1) is added portionwise over 15 min. The mixture is filtered and concentrated under a vacuum to afford the title compound as a colorless oil (17.54 g, 90%). LC-ES/MS m/z 284 (M+1).

PREPARATION 3

(2 S)—N-Benzyl-4-methoxy-N-[(1S)-1-phenylethyl] butan-2-amine

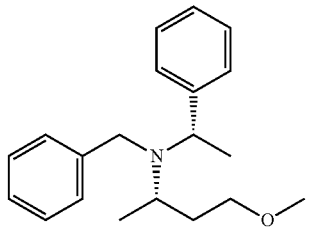

(3S)-3-[Benzyl-[(1S)-1-phenylethyl]amino]butan-1-ol (17.54 g, 61.9 mmol) is dissolved in anhydrous THF (186 mL) and cooled to 0° C. under an argon atmosphere. Sodium hydride (4.95 g, 60% suspension in mineral oil, 123.8 mmol) is added portionwise over 10 min. The mixture is stirred at 0° C. for 15 min, and then allowed to warm to RT. Methyl iodide (10.54 g, 74.28 mmol) is added dropwise over 30 min. After stirring for 30 additional min, the reaction is quenched by the addition of a saturated solution of NH$_4$Cl in water. The layers are separated and the aqueous layer is extracted with diethyl ether (2×100 mL). The combined organic layers are dried over MgSO$_4$, concentrated, and the crude is purified by normal phase chromatography (two 120 g silica-gel cartridges, 10% of methyl tert-butyl ether in hexanes) to afford the title compound as a colorless oil (14.96 g, 81%). LC-ES/MS m/z 298 (M+1).

PREPARATION 4

(S)-4-methoxybutan-2-amine hydrochloride

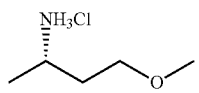

(2S)—N-Benzyl-4-methoxy-N-[(1S)-1-phenylethyl]butan-2-amine (14.96 g, 50.29 mmol) is dissolved in methanol (400 mL). The solution is deoxygenated by bubbling nitrogen through it. 20% Palladium hydroxide on carbon (1.50 g) is added to the solution and the resulting suspension is saturated with hydrogen and stirred under a hydrogen atmosphere for 16 h. The main product present at this time is the mono de-benzylated product. The suspension is filtered through a pad of CELITE®, and 1.1 g of 20% palladium hydroxide on carbon is added to the resulting solution. The suspension is stirred for 24 h under a hydrogen atmosphere. The suspension is filtered through a pad of CELITE®, and a 2 N solution of HCl in diethyl ether (60 mL) is added to the mixture and stirred for 30 min. The solution is concentrated under reduced pressure to afford the title compound as a white solid (7.01 g, 99%). $^1$H NMR (400 MHz, CDCl$_3$); δ 1.48 (3H, d, J=6.8 Hz), 1.8-1.9 (1H, m), 2.0-2.1 (1H, m), 3.37 (3H, s), 3.5-3.7 (3H, m), 8.3 (3H, br).

PREPARATION 5

(R)—N-[(1S)-3-Methoxy-1-methyl-propyl]-2-methyl-propane-2-sulfinamide

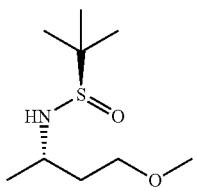

The following procedure is adapted from Ellman, J. A. et al J. Org. Chem. 2007, 72, 626-629.

To a 1 N solution of HCl (7.0 mL, 7.00 mmol) is added 1,3,3-trimethoxybutane (53.19 mL, 337.38 mmol) dropwise, and the resulting solution is heated to 50° C. and stirred for 30 min. Sodium bicarbonate (16.50 g, 196.41 mmol) is added to the mixture, previously cooled to RT, followed by diethyl ether and MgSO$_4$. Filtration followed by evaporation of the solvent affords the keto-ether intermediate, 4-methoxybutan-2-one as a yellow oil. The oil is added to a solution of (R)-(+)-2-methyl-2-propanesulfinamide (36.80 g, 303.64 mmol) and titanium (IV) ethoxide (123.14 g, 539.80 mmol) in THF (482 mL) at 25° C. under a nitrogen atmosphere. The resulting yellow suspension is heated to 60° C. and stirred at that temperature for 16 h. The reaction mixture is cooled to RT and then to −48° C. 1.0 M Lithium tri(sec-butyl)borohydride in THF (539.80 mL, 539.80 mmol) is added dropwise. The reaction mixture is allowed to warm to RT. After 1 h, the reaction mixture is cooled to 0° C. and methanol (1100 mL) is added while being rapidly stirred until gas evolution is no longer observed. The resulting suspension is filtered through a plug of CELITE®, and the filter cake is washed with ethyl acetate. The filtrate is washed with brine, and the brine layer is extracted twice with ethyl acetate. The combined organic layers are dried over Na$_2$SO$_4$, filtered and evaporated to a yellow oil.

The crude is adsorbed onto silica gel and purified through a silica gel column using a hexane/ethyl acetate gradient (from 7:1 to 100% ethyl acetate) to afford the desired product. Other fractions, containing an apolar impurity and the desired product are collected and purified again by silica gel chromatography. The apolar impurity is removed with hexane/ethyl acetate, 4:1. The desired product is eluted with dichloromethane/methanol, 95:5 to obtain additional material. The two batches of material are combined to give 38 g (54%) which is a ratio of about 3:1 of the desired/undesired diastereomer as seen by LCMS.

The material (38 g) is combined with another lot of material (23 g) that is made using the same general procedure and the diastereomers (3:1 ratio, 61 g) are separated by chiral phase high performance liquid chromatography (Stationary phase: OD-H; Column Size: (20 μm, 80×250 mm); Elution mode: isocratic; Mobile phase: hexane/isopropanol; Flow rate: 300 mL/min; UV detection: 215.16 nm; Loading: 4 g/6 min. The first eluting peak is the minor diastereomer, T$_R$=4.75 min. The second eluting peak is the major diastereomer (titled compound), T$_R$=6.61 min. The title compound is obtained as a slight yellow oil (43.5 g) from the chiral chromatography. ES/MS m/z 208 (M+1); >98% ee.

PREPARATION 6

(S)-4-methoxybutan-2-amine hydrochloride

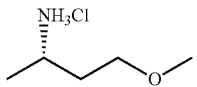

Hydrogen chloride, 4.0 M in dioxane (110.15 g, 419.61 mmol) is added to a solution of (R)—N-[(1S)-3-methoxy-1-methyl-propyl]-2-methyl-propane-2-sulfinamide (43.5 g, 209.80 mmol) in 1,4-dioxane (109 mL) at 0° C. and the reaction mixture is stirred for 1 h at RT. The solvent is concentrated under reduced pressure, the residue is re-suspended in toluene and the solvent is evaporated under reduced pressure. The residue is dried under vacuum for 15 min. THF is added and a white solid precipitates. The white solid is filtered off, washed with THF, allowed to dry and collected to afford the title compound (25.4 g, 87%).

The absolute configuration of the amine can be confirmed by derivatization with (S)-(−)-α-methoxy-α-trifluoromethylphenyl-acetic acid and comparison of the NMR with the same derivative of the (S)-4-methoxybutan-2-amine of Preparation 4 obtained from the chiral route.

PREPARATION 7

(3S)-3-Isothiocyanato-1-methoxy-butane

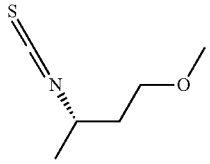

(S)-4-Methoxybutan-2-amine hydrochloride (25.4 g, 181.92 mmol) is suspended in THF (609 mL) and triethylamine (TEA, 32.17 mL, 230.78 mmol) is added. 1,1'-Thiocarbonyldiimidazole (46.74 g, 251.76 mmol) is added to the white suspension (slightly exothermic reaction) and the resulting yellow suspension is stirred under a nitrogen atmosphere overnight. Ethyl acetate (500 mL) is added to the yellow suspension, followed by 1 N HCl (500 mL). The organic phase is separated and washed with 1 N HCl (3×200 mL), water (200 mL), and brine (200 mL), dried over $Na_2SO_4$, filtered and concentrated under reduced pressure to afford the title compound (25.3 g, 83%) as a yellow oil. $^1$H NMR (400 MHz, $CDCl_3$); δ 1.37 (3H, d, J=6.6 Hz), 1.83 (2H, q, J=6.6 Hz), 3.35 (3H, s), 3.6-3.4 (2H, m), 3.99 (1H, six, J=6.6 Hz).

PREPARATION 8

Methyl 2,2-dimethyl-3-oxo-propanoate

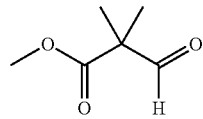

Methyl 3-hydroxy-2,2-dimethyl-propanoate (52.4 g, 396.49 mmol) is dissolved in dichloromethane (495 mL) and the mixture is cooled in an ice-water bath. Trichloroisocyanuric acid (101.36 g, 436.14 mmol) is added portionwise, followed by 2,2,6,6-tetramethylpiperidine-N-oxide (6.20 g, 39.65 mmol). The mixture is stirred at 0° C. for 15 min and then allowed to warm to RT and stirred for an additional 60 min. The solid is then filtered through CELITE® and rinsed with dichloromethane (300 mL). The filtrate is washed with a saturated solution of $Na_2CO_3$ in water. The organic phase is dried over $Na_2SO_4$, filtered, and concentrated under reduced pressure to afford the title compound (41.24 g, 80%) as a greenish oil. The product is used without further purification in the next reaction step. $^1$H NMR (400 MHz, $CDCl_3$); δ 1.34 (6H, s), 1.34 (6H, s), 3.74 (3H, s), 9.64 (1H, s).

PREPARATION 9

6-[2-(2,4-Difluorophenyl)ethynyl]-3-nitro-pyridin-2-amine

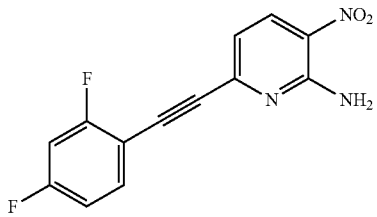

6-Chloro-3-nitro-pyridin-2-ylamine (1254 g, 7.23 mol), triethylamine (1510 mL, 10.84 mol) and acetonitrile (10 L) are charged into a 20 L, 4-neck round bottom flask equipped with a mechanical stirrer under nitrogen. To the resulting yellow suspension, copper(I) iodide (13.9 g, 72.3 mmol) and bis(triphenylphosphine)palladium (II) chloride (50.72 g, 72.3 mmol) are added. The resulting pale orange suspension is cooled to 0-5° C. and then degassed during 10 min with nitrogen. A solution of 1-ethynyl-2,4-difluoro-benzene (1100 g, 7.95 mol) dissolved in acetonitrile (2.5 L) is added dropwise during 60 min. The resulting mixture is left stirring at RT (30° C.) overnight. The mixture is cooled to 0-5° C. Toluene (6 L) is added to the suspension and the mixture is stirred for 45 min and filtered though a frit. The solid is washed with toluene (3×3 L), water (2×3 L) and is dried overnight in a vacuum oven, to obtain the title compound as a yellow solid (1750 g, 92%). LC-ES/MS m/z 276 (M+1).

PREPARATION 10

1-(6-Amino-5-nitro-2-pyridyl)-2-(2,4-difluorophenyl)ethane-1,2-dione

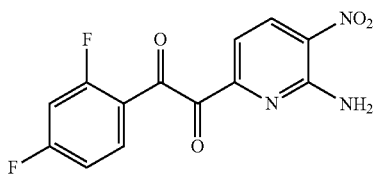

To a cold suspension (0-10° C.) of 6-[2-(2,4-difluorophenyl)ethynyl]-3-nitro-pyridin-2-amine (500 g, 1.82 mol) in acetone (10 L), is added cold buffer [$NaH_2PO_4$ (0.8 M)/$Na_2HPO_4$ (0.8 M)=85/15 (V/V)] (pH=6.0; 0-10° C.; 10 L). The temperature is maintained at 15° C. Potassium permanganate (1035 g, 6.55 mol) is added portionwise (3 portions). The mixture is stirred for 4 h at 15° C. The pH is adjusted to pH=5.0 and the temperature is kept below 15° C. A 28% sodium thiosulfate solution (2054 mL, 3.64 mol) is added slowly, maintaining the temperature below 15° C. and the pH below 7.5. Brine (7.5 L) and a mixture of methyl tert-butyl ether (3.75 L) and ethyl acetate (3.75 L) are added to the suspension. The mixture is stirred for 15 min at 13° C. The two phases are separated and the aqueous brown suspension is extracted twice with methyl tert-butyl ether (3.5 L). The combined organic layers are collected and washed with brine (2×3 L), dried over $Na_2SO_4$, filtered, and the solvent is evaporated under reduced pressure to obtain the title compound as a yellow solid (375 g). The experiment is repeated under the same conditions twice more. The resulting batches are combined to afford 1080 g. LC-ES/MS m/z 308 (M+1).

PREPARATION 11

Methyl 2-[4-(6-amino-5-nitro-2-pyridyl)-5-(2,4-difluorophenyl)-1H-imidazol-2-yl]-2-methyl-propanoate

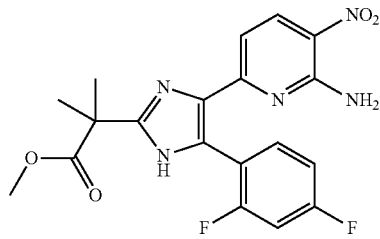

To a round bottom flask with a reflux condenser are added 1-(6-amino-5-nitro-2-pyridyl)-2-(2,4-difluorophenyl)ethane-1,2-dione (50 g, 162.75 mmol), ammonium acetate (126.72 g, 1.63 mol), methyl 2,2-dimethyl-3-oxo-propanoate (42.36 g, 325.51 mmol) and 1,4 dioxane (163 mL). The reaction mixture is heated to 80° C. during 1.5 h. The initial orange solution becomes dark with heating. The reaction mixture is concentrated under reduced pressure to eliminate the dioxane and the residue is dried under a high vacuum overnight. The residue is re-dissolved in ethyl acetate (800 mL) and extracted with a 2 M solution of $Na_2CO_3$ in water. The organic phase is dried over $MgSO_4$, concentrated, and dried under a high vacuum overnight to afford the title compound as a crude orange solid (80 g) that is used in the next step without further purification. LC-ES/MS m/z 418 (M+1).

PREPARATION 12

Methyl 2-[5-(2,4-difluorophenyl)-4-(6-hydroxy-5-nitro-2-pyridyl)-1H-imidazol-2-yl]-2-methyl-propanoate

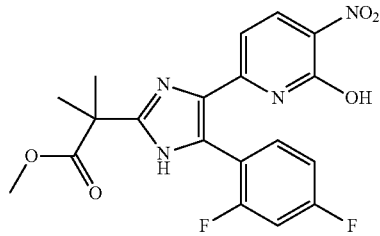

To a solution of methyl 2-[4-(6-amino-5-nitro-2-pyridyl)-5-(2,4-difluorophenyl)-1H-imidazol-2-yl]-2-methyl-propanoate (56 g, 134.17 mmol) in dimethyl sulfoxide (DMSO, 400 mL) and water (320 mL), is added sulfuric acid 95-97% (80 mL) dropwise. Then the mixture is cooled to 0° C. To the above mixture a solution of sodium nitrite (18.70 g, 268.35 mmol) in water (80 mL) is added dropwise over 15 min at 0° C. The reaction mixture is stirred for 20 min at that temperature and then the cooling bath is removed and the temperature is allowed to rise to RT. To the reaction mixture is added a 0.8 M aqueous solution of buffered sodium phosphate monobasic (1200 mL, pH=6). A yellow suspension appears. This suspension is stirred at RT for 1 h. The solid is filtered, washed with water, and dried in the oven to afford the title compound as an orange solid (49.5 g, 88%). LC-ES/MS m/z 419 (M+1).

PREPARATION 13

Methyl 2-[4-(5-amino-6-hydroxy-2-pyridyl)-5-(2,4-difluorophenyl)-1H-imidazol-2-yl]-2-methyl-propanoate

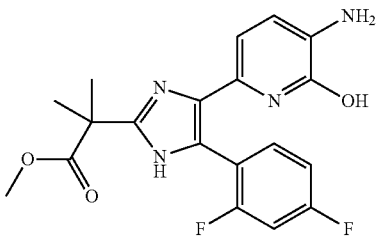

A mixture of methyl 2-[5-(2,4-difluorophenyl)-4-(6-hydroxy-5-nitro-2-pyridyl)-1H-imidazol-2-yl]-2-methyl-propanoate (49.5 g, 118.32 mmol) and palladium 5% weight (dry basis) on activated carbon (4.95 g, 2.33 mmol) in methanol (1.18 L) is stirred under a hydrogen atmosphere (balloon) at RT overnight. The suspension is filtered through CELITE®, rinsed with methanol, and the filtrate is concentrated under reduced pressure to afford the crude title compound (39 g) as a brown solid.

The crude material (90 g, 231.74 mmol), from multiple runs, is purified as follows. The material is suspended in a 1:1 mixture of dichloromethane (450 mL) and ethyl acetate (450 mL). The suspension is stirred at RT overnight. The suspension is filtered off and the solid is washed with a 1:1 mixture of dichloromethane/ethyl acetate. The brown solid is allowed to dry and collected to give 67 g of the title compound with >98% purity by liquid chromatography mass spectrometry. LC-ES/MS m/z 389 (M+1).

PREPARATION 14

Methyl 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propanoate

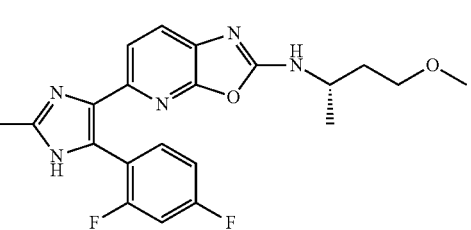

(3S)-3-Isothiocyanato-1-methoxy-butane (24.68 g, 169.94 mmol) is added to a suspension of methyl 2-[4-(5-amino-6-hydroxy-2-pyridyl)-5-(2,4-difluorophenyl)-1H-imidazol-2-yl]-2-methyl-propanoate (55 g, 141.62 mmol) in ethanol (550 mL) at RT. The reaction mixture is stirred under reflux overnight and then cooled to 50° C. Dicyclohexylcarbodiimide (37.99 g, 184.10 mmol) is added to the mixture and the resulting suspension is stirred under reflux for 20 h. The reaction is allowed to reach RT and the solvent evaporated under reduced pressure. The residue is absorbed in silica gel and purified through a silica gel column (first using dichloromethane as an eluent to remove the most apolar impurities and then with dichloromethane/methanol 95:5 to elute the desired product) to afford the title compound (52 g, 74%) as a dark brown foam. LC-ES/MS m/z 500 (M+1).

PREPARATION 15

2-[(1S)-2-Hydroxy-1-methyl-ethyl]isoindoline-1,3-dione

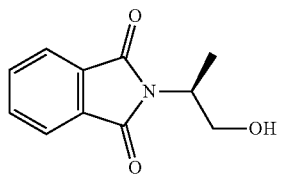

A mixture of (2S)-2-aminopropan-1-ol (26 mL, 333 mmol) and phthalic anhydride (51.7 g, 349.4 mmol) is heated at 140° C. overnight. During this time the solid becomes an orange liquid. The reaction is cooled to RT and diluted with ethyl acetate (10 mL/g). The organic phase is washed with saturated $NaHCO_3$ and 10% citric acid, dried over $MgSO_4$, filtered, and concentrated to afford the title compound (68.3 g, 98%) as a white solid that is used without further purification. LC-ES/MS m/z 206 (M+1).

PREPARATION 16

2-[(1S)-2-Ethoxy-1-methyl-ethyl]isoindoline-1,3-dione

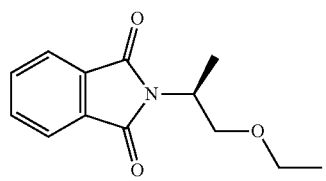

To a solution of 2-[(1S)-2-hydroxy-1-methyl-ethyl]isoindoline-1,3-dione (47 g, 229 mmol) and iodoethane (89.3 g, 572.5 mmol) in THF (376 mL) is added potassium tert-butoxide (64.25 g, 572.5 mmol) in one portion. The mixture is stirred under a nitrogen atmosphere for 15 h. The mixture is diluted with ethyl acetate (200 mL) and washed with brine (200 mL). The aqueous phase is extracted with ethyl acetate (2×100 mL). The combined organic extracts are dried over $MgSO_4$, filtered, concentrated under reduced pressure, and then dried under high vacuum to afford the title compound (39.4 g, 74%) as an orange solid that is used without further purification. LC-ES/MS m/z 234 (M+1).

PREPARATION 17

(2S)-1-Ethoxypropan-2-amine hydrochloride

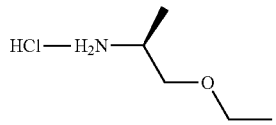

2-[(1S)-2-Ethoxy-1-methyl-ethyl]isoindoline-1,3-dione (12.84 g, 55 mmol) is dissolved in methanol (120 mL). Hydrazine monohydrate (6.9 mL, 138 mmol) is added slowly and the mixture is stirred at 40° C. for 4 h (a white solid is formed). NaOH (1 mL) is added and the pH rises to 13-14. The solid is filtered and washed with dichloromethane. The filtrate layers are separated and the aqueous layer further extracted with dichloromethane. The combined organic layers are dried over $MgSO_4$ and filtered. 2 N HCl in ether (70 mL, 140 mmol) is added to the solution. The mixture is stirred for 15 min and the solvent evaporated under reduced pressure to give the title compound as a white solid (6.61 g, 86%). $^1$H NMR (400 MHz, $CD_3OD$); δ 1.22 (t, 3 H, J=7.02 Hz), 1.28 (d, 3 H, J=6.52 Hz), 3.42 (m, 2H), 3.58 (m, 3H).

PREPARATION 18

(2S)-1-Ethoxy-2-isothiocyanato-propane

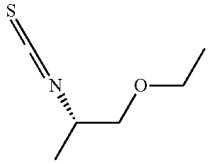

To a solution of (2S)-1-ethoxypropan-2-amine hydrochloride (2 g, 12.03 mmol) in dimethylformamide (DMF, 20 mL) and TEA (1.85 mL, 13.24 mmol) is added 1,1'-thiocarbonyldiimidazole (2.36 g, 13.24 mmol). The mixture is stirred under a nitrogen atmosphere for 16 h. The mixture is diluted with ethyl acetate and washed thoroughly with 1 N HCl, water, and brine, dried over $MgSO_4$, and concentrated under reduced pressure (bath temperature not to exceed 20° C. to avoid product evaporation) to obtain crude material (1.84 g) containing the title compound that is used as is without further purification. $^1$H NMR (400 MHz, $CDCl_3$); δ 1.26 (t, 3H, J=7.13 Hz), 1.33 (d, 2H, J=6.63 Hz), 3.46 (dd, J=5.86, 1.62 Hz, 2H), 3.55 (dd, J=13.98, 6.97 Hz, 2H), 3.93 (m, 1H).

PREPARATION 19

3-Methyloxetane-3-carbaldehyde

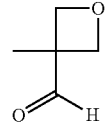

(3-Methyloxetan-3-yl)methanol (6.0 g, 58.75 mmol) is dissolved in dichloromethane (117 mL). Trichloroisocyanuric acid (13.93 g, 59.92 mmol) is added portionwise at −5° C. followed by the addition of 2,2,6,6-tetramethylpiperidine-1-oxyl (TEMPO) (0.92 g, 5.87 mmol). The reaction mixture is stirred at −5° C. for 20 min, allowed to warm to RT, and stirred for 20 additional min. The mixture is filtered through a pad of CELITE®, diluted with dichloromethane (200 mL), and washed with saturated aqueous $Na_2CO_3$ (100 mL), 1 N HCl (100 mL) and brine (50 mL). The organic portion is concentrated to afford the title compound as an orange oil (4.17 g, 71%) that is used without further purification. $^1$H NMR (400 MHz, $CDCl_3$); δ 1.48 (s, 3H), 4.50 (d, 2H, J=6.34 Hz), 4.88 (d, 2H, J=6.34 Hz), 9.95 (s, 1H).

Alternate Preparation:

Potassium bromide (11.65 g, 0.098 mol) is added to a mixture of (3-methyloxetan-3-yl)methanol (200 g, 1.96 mol) and TEMPO (3.06 g, 0.019 mol) in dichloromethane (2 L) at 0° C. Then, an aqueous solution of 10% sodium hypochlorite (1.6 L, 2.35 mol), adjusted to pH=9 with solid $NaHCO_3$, is added dropwise to the above solution (3 h addition, internal temperature kept <10° C.). The resulting mixture is stirred for 15 min and the two phases are separated. The aqueous phase is extracted with a 10% 2-propanol/dichloromethane mixture until no product is detectable by thin layer chromatography in the aqueous phase. The combined organic phases are washed with saturated sodium thiosulphate solution, dried over $MgSO_4$, filtered, and concentrated to afford the title compound as an orange oil (114 g, 58%).

PREPARATION 20

1-Methoxycarbonylcyclopropanecarboxylic acid

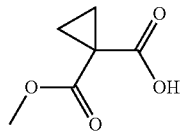

Dimethyl cyclopropane-1,1-dicarboxylate (26.08 mL, 189.87 mmol) is dissolved in methanol (319 mL) and the solution is cooled to 0° C. 1 N NaOH (190 mL, 190 mmol, 1 eq) in water is added dropwise. The resulting mixture is stirred at RT overnight. The solution is concentrated under reduced pressure to remove the methanol and the resulting aqueous solution is washed with dichloromethane (3×50 mL) and acidified with 1 N HCl (pH=2-3). The solution is then extracted with ethyl acetate (5×100 mL) and dichloromethane (3×50 mL). The combined organic portions are dried over $MgSO_4$, filtered, and concentrated to afford the title compound (16.4 g, 60%). $^1$H NMR (400 MHz, $CDCl_3$); δ 1.9-1.7 (m, 4H), 3.78 (s, 3H).

PREPARATION 21

Methyl 1-(hydroxymethyl)cyclopropanecarboxylate

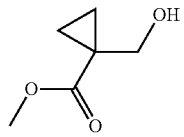

1-Methoxycarbonylcyclopropane carboxylic acid (16.4 g, 113.89 mmol), TEA (17.6 mL, 127.55 mmol), and THF (325 mL) are charged in a round bottom flask. The mixture is cooled to −10° C. and isobutyl chloroformate (16.5 mL, 127.55 mmol) is added dropwise. The solution is stirred for 1 h. In a separate flask, sodium borohydride (13 g, 341.67 mmol) is dissolved in a mixture of THF (165 mL) and water (40 mL) and cooled in an ice bath. The insoluble material is removed by filtration from the first solution. To the borohydride solution is added the 1-methoxycarbonylcyclopropane carboxylic acid solution described above, dropwise over a period of 1.5 h. The resulting solution is stirred at the same temperature for 1 h. The reaction mixture is poured into a cooled 20% aqueous solution of citric acid and extracted with ethyl acetate (3×150 mL). The combined organic layers are washed with brine, dried over $MgSO_4$, filtered, and concentrated under reduced pressure to afford the title compound (13.5 g, 91%). $^1$H NMR (400 MHz, $CDCl_3$); δ 0.9-0.8 (m, 2H), 1.3-1.2 (m, 2H), 3.62 (s, 2H) 3.69 (s, 3H).

PREPARATION 22

Methyl 1-formylcyclopropanecarboxylate

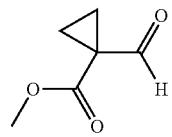

Methyl 1-(hydroxymethyl)cyclopropanecarboxylate (16.0 g, 123.07 mmol) is dissolved in dichloromethane (320 mL) and the mixture is cooled to −5° C. Trichloroisocyanuric acid (29.1 g, 125.5 mmol) is added portionwise followed by the addition of TEMPO (1.9 g, 12.3 mmol). The reaction mixture is stirred at −5° C. for 20 min, allowed to warm to RT, and stirred for 20 min. The mixture is filtered through a pad of CELITE® and diluted with dichloromethane (500 mL). The solution is washed with saturated $Na_2CO_3$ (300 mL), 1 N HCl (300 mL), brine (300 mL), and saturated ammonium chloride (3×200 mL). The organic portion is dried over $MgSO_4$, filtered, and concentrated under reduced pressure to obtain 19 g of the title compound, still containing dichloromethane (theoretical 15.75 g). The material is used as is in the next reaction. $^1$H NMR (400 MHz, $CDCl_3$); δ 1.7-1.6 (m, 4H), 3.81 (s, 3H), 10.38 (s, 1H).

PREPARATION 23

6-[2-Cyclopropyl-5-(2,4-difluorophenyl)-1H-imidazol-4-yl]-3-nitro-pyridin-2-amine

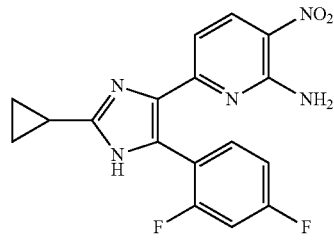

A KIMAX® tube is charged with 1-(6-amino-5-nitro-2-pyridyl)-2-(2,4-difluorophenyl)ethane-1,2-dione (5 g, 16.28 mmol), 1,4-dioxane (50 mL), and ammonium acetate (6.27 g, 81.38 mmol). Cyclopropanecarbaldehyde (3.42 mL, 48.83 mmol) is added dropwise to the mixture. The resulting mixture is purged with nitrogen, the tube is sealed, and it is heated at 80° C. overnight; after which the mixture is allowed to cool to RT. The mixture is then concentrated to dryness under reduced pressure. Ethyl acetate (700 mL) and saturated $NaHCO_3$ aqueous solution are added. The organic layer is separated, washed with brine (3×250 mL), dried over $MgSO_4$, and concentrated to afford the crude title compound (5.5 g) which is used in the next step without further purification. LC-ES/MS m/z 358 (M+1).

Prepare the intermediates in the table below, by essentially following the procedure as described in Preparation 23, using 1-(6-amino-5-nitro-2-pyridyl)-2-(2,4-difluorophenyl)ethane-1,2-dione and the appropriate aldehyde as starting materials.

| Prep | Structure | Chemical Name | LC-ES/MS m/z |
|---|---|---|---|
| 24* | 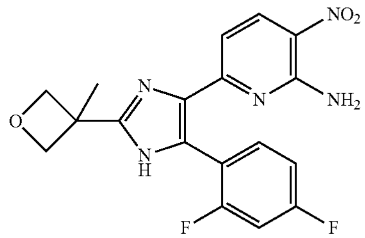 | 6-[5-(2,4-Difluorophenyl)-2-(3-methyloxetan-3-yl)-1H-imidazol-4-yl]-3-nitro-pyridin-2-amine | 388 (M + 1) |
| 25 | 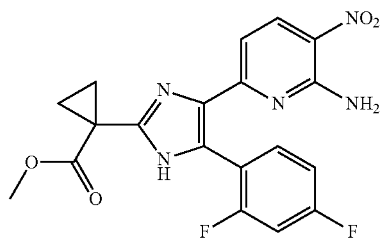 | Methyl 1-[4-(6-amino-5-nitro-2-pyridyl)-5-(2,4-difluorophenyl)-1H-imidazol-2-yl]cyclopropanecarboxylate | 416 (M + 1) |

*Reaction is run at 90° C. for 1.5 h. During workup a solid precipitates and is collected from addition of bicarbonate solution. The filtrate is worked up as before to obtain a red oil. The oil is sonicated in a 4:1 mixture of ethyl acetate/hexane to obtain a suspension which is filtered.

PREPARATION 26

6-[2-Cyclopropyl-5-(2,4-difluorophenyl)-1H-imidazol-4-yl]-3-nitro-pyridin-2-ol

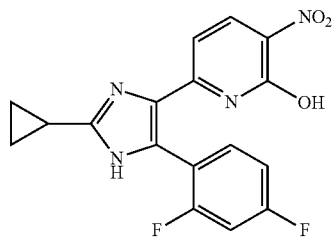

6-[2-Cyclopropyl-5-(2,4-difluorophenyl)-1H-imidazol-4-yl]-3-nitro-pyridin-2-amine (5.51 g, 15.41 mmol) is suspended in dimethyl sulfoxide (DMSO, 32 mL), water (25 mL), and concentrated $H_2SO_4$ (6 mL). The suspension is cooled at 0° C. and sodium nitrite (2.13 g, 30.81 mmol) is added portionwise at such a rate that the temperature is maintained below 5° C. The mixture is stirred at 0° C. for 30 min, and then is allowed to warm to RT, and is stirred until liquid chromatography/mass spectrometry (LC/MS) shows complete conversion of the starting material (1 hour). A 0.8 M aqueous solution of sodium phosphate monobasic (200 mL) is added to the mixture. A yellow suspension is formed. Aqueous 1 N NaOH is then added until the pH rises to 8. The mixture is stirred for 30 h, filtered, and the solid is rinsed with water, and then dried under reduced pressure to afford the title compound (4.53 g, 82%). LC-ES/MS m/z 358.9 (M+1).

Prepare the intermediates in the table below, by essentially following the procedure as described in Preparation 26, using the appropriate 3-nitro-pyridin-2-amine as starting material.

| Prep | Structure | Chemical name | LC-ES/MS m/z |
|---|---|---|---|
| 27 | 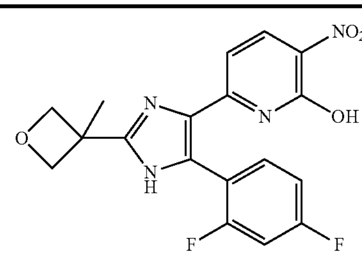 | 6-[5-(2,4-Difluorophenyl)-2-(3-methyloxetan-3-yl)-1H-imidazol-4-yl]-3-nitro-pyridin-2-ol | 389.1 (M + 1) |

| Prep | Structure | Chemical name | LC-ES/MS m/z |
|---|---|---|---|
| 28 | 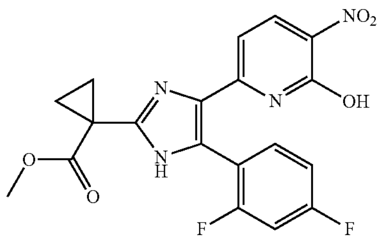 | Methyl 1-[5-(2,4-difluorophenyl)-4-(6-hydroxy-5-nitro-2-pyridyl)-1H-imidazol-2-yl]cyclopropanecarboxylate | 417 (M + 1) |

PREPARATION 29

3-Amino-6-[2-cyclopropyl-5-(2,4-difluorophenyl)-1H-imidazol-4-yl]pyridin-2-ol

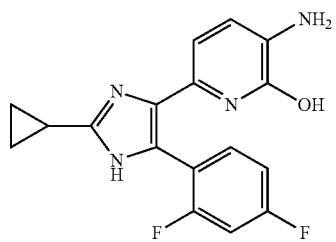

6-[2-Cyclopropyl-5-(2,4-difluorophenyl)-1H-imidazol-4-yl]-3-nitro-pyridin-2-ol (4.525 g, 12.63 mmol) is dissolved in ethanol (63 mL). The solution is degassed with bubbling nitrogen gas. 10% Pd/C (920 mg) is added portionwise to the mixture and the mixture is saturated with hydrogen. The mixture is stirred under a hydrogen atmosphere (balloon) at RT over the weekend, at which time LC/MS shows complete conversion. The suspension is filtered through a pad of CELITE® to remove the catalyst and the solution is concentrated under reduced pressure to afford the title compound (3.97 g, 89%). LC-ES/MS m/z 328.9 (M+1).

Prepare the intermediates in the table below, by essentially following the procedure as described in Preparation 29, using the appropriate 3-nitro-pyridinol as starting material.

| Prep | Structure | Chemical Name | LC-ES/MS m/z |
|---|---|---|---|
| 30 | 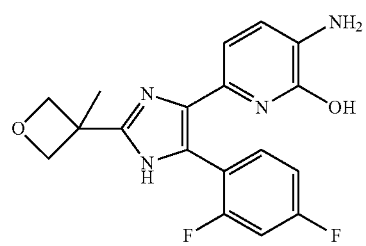 | 3-Amino-6-[5-(2,4-difluorophenyl)-2-(3-methyloxetan-3-yl)-1H-imidazol-4-yl]pyridin-2-ol | 359 (M + 1) |
| 31 | 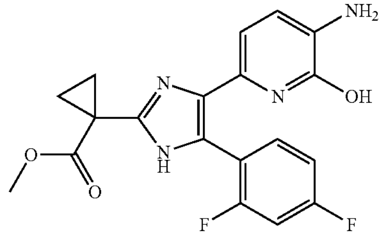 | Methyl 1-[4-(5-amino-6-hydroxy-2-pyridyl)-5-(2,4-difluorophenyl)-1H-imidazol-2-yl]cyclopropanecarboxylate | 387 (M + 1) |

PREPARATION 32

Methyl 1-[5-(2,4-difluorophenyl)-4-[2-[[(1S)-2-ethoxy-1-methyl-ethyl]amino]oxazolo[5,4-b]pyridin-5-yl]-1H-imidazol-2-yl]cyclopropanecarboxylate

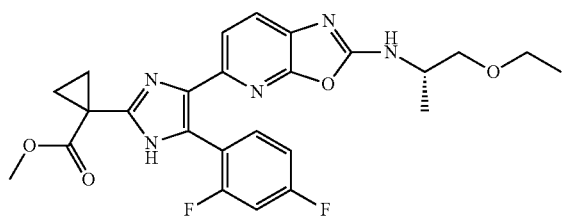

A mixture of methyl 1-[4-(5-amino-6-hydroxy-2-pyridyl)-5-(2,4-difluorophenyl)-1H-imidazol-2-yl]cyclopropanecarboxylate (4 g, 10.35 mmol) and (2S)-1-ethoxy-2-isothiocyanato-propane (2.379 g, 15.53 mmol) are dissolved in ethanol (34 mL). The mixture is heated to 85° C. in a sealed flask for 16 h. Diisopropyl carbodiimide (3.21 g, 20.71 mmol) is added dropwise and the mixture is stirred at 85° C. for 16 h, after which time an additional 3 g of diisopropyl carbodiimide is added and the mixture is heated at 85° C. for an additional 4 h. The solvent is evaporated and the residue is purified by normal phase chromatography (120 g silica-gel cartridge, using a hexane-ethanol gradient to afford the title compound (1.180 g, 24%). LC-ES/MS m/z 498.1 (M+1).

PREPARATIONS FOR SYNTHESIS OF EXAMPLE 1 ALTERNATE

PREPARATION 33

(S)—N-[(1S)-3-Methoxy-1-methyl-propyl]-2-methyl-propane-2-sulfinamide

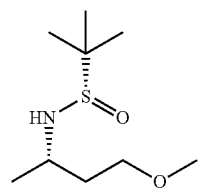

For a comparison of L-Selectride verses sodium borohydride in the reduction of N-tert-butanesulfinyl imines see Faul, M. M. *J. Org. Chem.* 2007, 71, 6859-6862.

1,3,3-Trimethoxybutane (145.4 g, 0.98 mol) is combined with 1 N aqueous hydrochloric acid (50.0 mL, 0.05 mol) and stirred for 1-2 h at RT under a nitrogen atmosphere. THF (1.5 L) is added and the solvent is evaporated at standard atmospheric pressure below 70° C. twice. THF (1.5 L) is added to prepare a solution of 4-methoxybutan-2-one in THF. (S)-(−)-2-Methyl-2-propanesulfinamide (124.4 g, 1.03 mol) and titanium (IV) ethoxide (447.0 g, 1.96 mol) are added and the reaction heated to 65-70° C. for 16-17 h. The reaction mixture is cooled to −10 to 0° C. Sodium borohydride (37.0 g, 0.98 mol) is added in portions, and then the mixture is stirred for 1-2 h at the same temperature. The reaction mixture is warmed to RT and stirred for 1-2 h. It is then cooled to 10-20° C. and methanol (100 mL) is added dropwise over 1-2 h. 25% Aqueous sodium chloride (300 mL) is added and the mixture is warmed to RT. Ethyl acetate (500 mL) is added. The mixture is stirred for 1-2 h at RT and then filtered. The filtercake is rinsed with additional ethyl acetate (807 mL). The layers are separated and the organic phase is washed with 25% aqueous sodium chloride (1.0 L). The aqueous phase is extracted with ethyl acetate (500 mL). The organic portions are combined, and the solvent is distilled at atmospheric pressure (no vacuum) below 75° C. to arrive at a solution of 300-500 mL total volume. Ethyl acetate (600 mL) and sodium thiosulfate (150.0 g) are added and the mixture is stirred for 1-2 h at 20-30° C. The mixture is filtered and the filtrate is concentrated. The diastereomers are separated by supercritical fluid chromatography to afford the title compound as a yellow oil (205.0 g, 65%). Column. ChiralPak® AD 10 μm, 50×300 mm; Elution mode: Isocratic; Mobile phase: $CO_2$/ethanol; Flow rate: 280 mL/min; UV detection: 215.16 nm; Loading: 300 mg/mL. The first eluting peak is the minor diastereomer, $T_R$=15.17 min. The second eluting peak is the major diastereomer representing the title compound, $T_R$=17.11 min.

PREPARATION 34

(3S)-3-Isothiocyanato-1-methoxy-butane

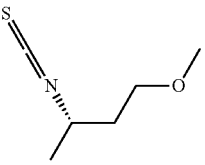

Under a nitrogen atmosphere are combined methanol (185 mL), THF (1.76 L), and N—S-[(1S)-3-methoxy-1-methyl-propyl]-2-methyl-propane-2-sulfinamide (220.0 g, 1.06 mol) and cooled to −10 to 0° C. Hydrochloric acid (1.26 L, 5.3 mol, 4.2 N in THF) is added dropwise and the temperature is maintained below 10° C. The reaction mixture is stirred for 3-4 h at 0-10° C., and is concentrated under reduced pressure below 45° C. to a solution volume of 400.0-600.0 mL. THF (880 mL) is added and the reaction mixture is concentrated under reduced pressure below 45° C. to a solution volume of 400-600 mL. The reaction mixture is cooled to 20-30° C. and stirred for 0.5-1 h. Seed crystals of (S)-4-methoxybutan-2-amine, hydrochloride are added (5.0 g, 35.8 mmol). (Seed crystals can be generated from the solids obtained from Preparations 4 or 6, or can be obtained using other methods common to one skilled in the art, such as recrystallization of a small aliquot.) Methyl tert-butyl ether (660 mL) is also added and the mixture is stirred at 20-25° C. for 2-4 h. The mixture is cooled to 0-5° C. and stirred for 2-4 h. The solids are collected by filtration and the filtercake is washed with methyl tert-butyl ether (110 mL). The solids are transferred to a reaction vessel and methyl tert-butyl ether (660 mL) is added at RT. Sodium thiosulfate (270.0 g, 1.9 mol) and sodium hydroxide (42.5 g, 1.06 mol) are added and the mixture is stirred for 1-2 h at 10-20° C. The mixture is filtered and the filtercake is washed with methyl tert-butyl ether (440 mL) to provide (S)-4-methoxybutan-2-amine as a crude solution in methyl tert-butyl ether (87.5 g). The material is used in the next reaction as follows.

Under a nitrogen atmosphere N,N-thiocarbonyldiimidazole (97.0 g, 0.55 mol) and THF (470 mL) are added and the mixture is stirred for 15-30 min. The mixture is cooled to −10 to 0° C., a solution of (S)-4-methoxybutan-2-amine (46.9 g, 0.455 mol) in methyl tert-butyl ether (389 mL) is added, and the reaction mixture is warmed to 10-20° C. The reaction mixture is stirred at this temperature for 15-20 h, and then is cooled to 0-10° C. Hydrochloric acid (275 mL, 4 N in water) is added to arrive at a pH of 1 to 2. The reaction mixture is warmed to RT and the layers are separated. The aqueous layer is extracted with ethyl acetate (235 mL) and the organic layers are combined and washed with water (140 mL). The organic solution is concentrated under reduced pressure below 45° C., ethyl acetate (211.5 mL) is added, and the solution is concentrated under reduced pressure below 45° C. twice, and ethyl acetate (235 mL) is added. Sodium thiosulfate (32.3 g, 227.0 mmol) is added, the solution is filtered, and the filtercake is washed with ethyl acetate (104 mL). The filtrate is concentrated under reduced pressure below 45° C. to furnish the title compound as a yellow oil (55.0 g, 77%).

PREPARATION 35

Methyl 2,2-dimethyl-3-oxo-propanoate

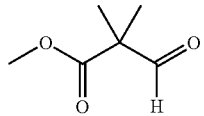

Methyl 3-hydroxy-2,2-dimethyl-propanoate (25.4 kg, 192.2 mol) and dichloromethane (241 L) are combined under a nitrogen atmosphere at RT with stirring. (2,2,6,6-Tetramethyl-piperidin-1-yl)oxyl (0.61 kg, 3.9 mol) is added and the reaction mixture is cooled to 0-5° C. Trichloroisocyanuric acid (31.2 kg, 134.5 mol) is added portionwise at 0-5° C. and the reaction mixture is stirred for 16-18 h at this temperature. The reaction is filtered and the filtercake is washed with dichloromethane (25.4 L) and the filtrate concentrated under reduced pressure below 50° C. 1,4-Dioxane (25.4 L) is added and the organic phase is concentrated under reduced pressure below 65° C. to obtain the title compound as a yellow liquid (127.8 kg, 77%) that is used without further purification.

PREPARATION 36

6-[2-(2,4-Difluorophenyl)ethynyl]-3-nitro-pyridin-2-amine

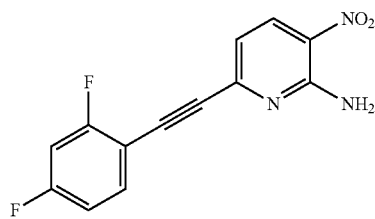

6-Chloro-3-nitro-pyridin-2-ylamine (16.2 kg, 93.3 mol), acetonitrile (130.8 L), cuprous iodide (0.18 kg, 1.0 mol), and bis(triphenylphosphine)palladium (II) chloride (0.66 kg, 0.9 mol) are combined under a nitrogen atmosphere at 20-25° C. with stirring. Triethylamine (19.7 L, 141.3 mol) is added and the mixture is heated to 30-35° C. A solution of 1-ethynyl-2,4-difluoro-benzene (18.0 kg, 130.3 mol) in acetonitrile (32.6 L) is added under a nitrogen atmosphere at 30-35° C. The mixture is stirred at 15-25° C. for 2-4 h. Toluene (80.0 L) is added and the mixture is stirred for 0.5-1 h, then cooled to 0-5° C. and stirred for 2-4 h. The reaction mixture is centrifuged and the filter cake is rinsed with toluene (2×64 L) and water (2×32.4 L). The solids are dried under reduced pressure below 50° C. to furnish the title compound as a yellow solid (21.7 kg, 83%).

PREPARATION 37

1-(6-Amino-5-nitro-2-pyridyl)-2-(2,4-difluorophenyl)ethane-1,2-dione

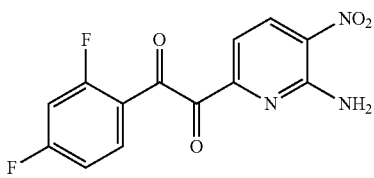

6-[2-(2,4-Difluorophenyl)ethynyl]-3-nitro-pyridin-2-amine (2.0 kg, 7.3 mol) and acetone (40.5 L) are added to a reactor under a nitrogen atmosphere and the mixture is cooled to 0-10° C. with stirring. A buffering solution of water (38.3 L), sodium dihydrogen phosphate (3.3 kg), and disodium hydrogen phosphate (0.7 kg) is added at 0-15° C. The mixture is cooled to 3-6° C. and is charged with solid potassium permanganate (4.1 kg, 25.9 mol) at 3-6° C. The mixture is stirred for 3 h to 5 h, and then portions of the reaction mixture are transferred to a vessel containing water (9.3 L) and sodium thiosulfate pentahydrate (3.6 kg) at 15-20° C. The mixture is stirred at 15-25° C. Water (50 L) is added and the mixture stirred for 0.5-1 h and is filtered. The filtrate is concentrated under reduced pressure below 45° C. When the distillation of solvent is complete, water (40 L) is added at 20-25° C. and the mixture is stirred for 0.5-1 h. The solids are collected by filtration and the filtercake is dried below 40° C. to obtain the title compound as a yellow solid (1.7 kg, 75%).

PREPARATION 38

Methyl 2-[4-(6-amino-5-nitro-2-pyridyl)-5-(2,4-difluorophenyl)-1H-imidazol-2-yl]-2-methyl-propanoate, methanesulfonate

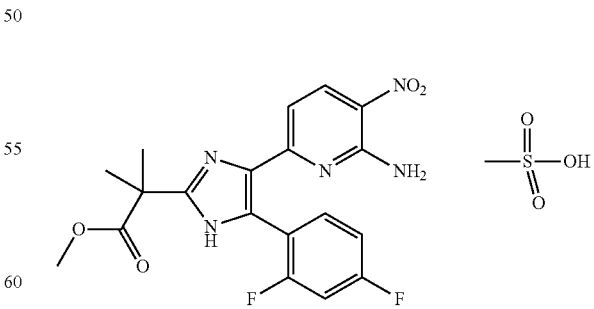

Ammonium acetate (30.0 kg, 389.2 mol), 1,4-dioxane (193.6 L), and methyl 2,2-dimethyl-3-oxo-propanoate (10.2 kg, 78.4 mol) are combined under a nitrogen atmosphere with stirring at 20-25° C. for 0.5-1 h. 1-(6-Amino-5-nitro-2-pyridyl)-2-(2,4-difluorophenyl)ethane-1,2-dione (18.5 kg, 60.2 mol) is added and the mixture is stirred for 10-14 h at 20-25° C. Toluene (36.9 L) is added and the solution concentrated under reduced pressure below 65° C. Toluene (76.8 L) is added and then the solution is concentrated under reduced pressure below 65° C. Toluene (36.9 L) and ethyl acetate (37.1 L) are added and the mixture is filtered. The filtrate is set aside and the filtercake is transferred into a separate reactor and ethyl acetate (37.1 L) is added. The mixture is heated to 50-60° C. with stirring for 20-30 min. The mixture is cooled to 20-25° C., filtered and the filtrate is combined with the previous filtrate. The combined filtrates are concentrated under reduced pressure below 60° C. and toluene (76.8 L) is added. The mixture is concentrated under reduced pressure below 65° C. Ethyl acetate (18.6 L) and toluene (18.3 L) are added and the solution heated to 50-70° C. Methanesulfonic acid (4.3 L, 66.2 mol) in ethyl acetate (18.6 L) is added and the reaction is stirred for 1-2 h. The reaction is cooled to 10-25° C. and is stirred for 2-5 h. The solids are collected by filtration, and the filtercake is washed with ethyl acetate (18.6 L) to provide the title compound as a brown solid (17.0 kg, 96.2% purity, 46.2% yield). $^1$H NMR (d$_6$-DMSO, 400 MHz) δ 1.69 (s, 6H), 2.36 (s, 3H), 3.68 (s, 3H), 6.89 (d, 1H, J=8.8 Hz), 7.00 (s, 1 H), 7.25 (s, 1H), 7.12 (s, 1H), 7.27 (dd, 1H, J=8.4 Hz, 1.6 Hz), 7.45 (ddd, 1H, J=10.0 Hz, 10.0 Hz, 2.4 Hz), 7.83-7.68 (m, 2 H), 8.40 (d, 1H, J=8.8 Hz).

PREPARATION 39

Methyl 2-[5-(2,4-difluorophenyl)-4-(6-hydroxy-5-nitro-2-pyridyl)-1H-imidazol-2-yl]-2-methyl-propanoate

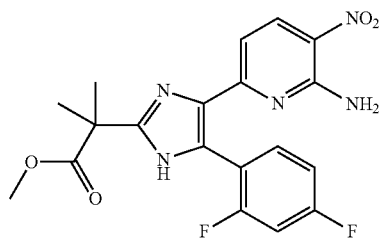

Under a nitrogen atmosphere methyl 2-[4-(6-amino-5-nitro-2-pyridyl)-5-(2,4-difluorophenyl)-1H-imidazol-2-yl]-2-methyl-propanoate methanesulfonate (68.9 g, 134.2 mmol), dimethyl sulfoxide (275.5 mL), THF (116.2 mL), and water (303.2 mL) are added and the mixture is stirred at 20-25° C. Sulfuric acid 95-97% (93.6 mL) is added dropwise to the reaction mixture and the temperature is maintained below 30° C. The reaction mixture is cooled to 0-5° C., and a solution of sodium nitrite (18.6 g, 0.27 mmol) in water (82.7 mL) is added at 0-10° C. The reaction mixture is stirred for 1-2 h at this temperature. 10% Aqueous sodium dihydrogen phosphate (930.0 mL) is added dropwise to maintain the temperature below 25° C. The resulting mixture is stirred for 2-3 h at 15-25° C., and the solids are collected by filtration. The filtercake is washed with water (138 mL) and the solids are transferred into a reaction vessel. Methanol (566 mL) is added and the mixture is heated to 60-65° C. for 1-2 h. Water (87 mL) is added and the mixture is stirred at 60-65° C. for 1-2 h. The reaction mixture is cooled to 15-25° C. and the mixture is stirred at 15-25° C. for 2-4 h. The mixture is filtered, the cake is washed with methanol (87 mL), and is dried under a vacuum below 70° C. to provide the title compound as a yellow solid (53.28 g, 93%).

PREPARATION 40

Methyl 2-[4-(5-amino-6-hydroxy-2-pyridyl)-5-(2,4-difluorophenyl)-1H-imidazol-2-yl]-2-methyl-propanoate

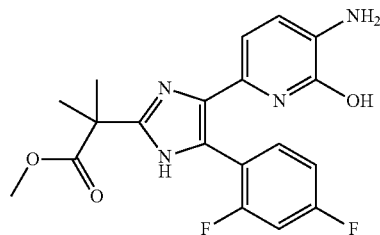

Methyl 2-[5-(2,4-difluorophenyl)-4-(6-hydroxy-5-nitro-2-pyridyl)-1H-imidazol-2-yl]-2-methyl-propanoate (90.0 g, 0.22 mol), wet 10% Pd/C (4.5 g), and methanol (1.77 L) are combined at 15-25° C. The reaction is stirred under 20-25 psig hydrogen atmosphere for 3-6 h. The reaction mixture is filtered over diatomaceous earth, and the filter aid is washed with methanol (227 mL). The filtrate is concentrated under reduced pressure below 40° C., and methyl tert-butyl ether (729.3 mL) is added. The MTBE is removed under reduced pressure below 40° C., and more methyl tert-butyl ether (729.3 mL) is added. The MTBE is removed under reduced pressure below 40° C. Methyl tert-butyl ether (182 mL) and methanol (46 mL) are added and the mixture heated to 50-60° C. for 1-2 h. The mixture is cooled to 10-15° C., and stirred for 2-4 h. The solids are collected by filtration and the filtercake washed with methyl tert-butyl ether (61 mL). The solids are dried under vacuum below 50° C. to furnish the title compound as a yellow solid (75.0 g, 88%).

PREPARATION 41

Methyl 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propanoate

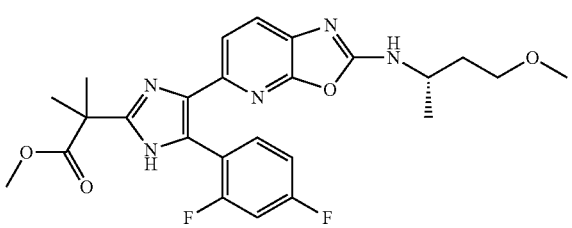

Dimethyl sulfoxide (713 mL) is degassed with nitrogen at 25-30° C. for 0.5-1 h under a nitrogen atmosphere. Methyl 2-[4-(5-amino-6-hydroxy-2-pyridyl)-5-(2,4-difluorophenyl)-1H-imidazol-2-yl]-2-methyl-propanoate (35.0 g, 90.0 mmol) and (3S)-3-isothiocyanato-1-methoxy-butane (19.58 g, 0.14 mol) are added and the reaction heated to 63-68° C. The reaction mixture is stirred for 18-24 h at this temperature and then add 1-ethyl-3-(3-dimethylaminopropyl)carbodiimide hydrochloride (19.3 g, 100.7 mmol) is added in portions. The reaction mixture is stirred for 2-4 h at 60-65° C. Additional 1-ethyl-3-(3-dimethylaminopropyl)carbodiimide hydrochloride (1.9 g, 9.9 mmol) is added if the reaction does not reach complete conversion. The reaction mixture is cooled to 20-30° C. and is filtered over diatomaceous earth. Ethyl acetate (351 mL) and water (350 mL) are added to the filtrate. The layers are separated and the aqueous phase extracted with ethyl acetate (312 mL). The organic layers are combined and washed with water (2×210 mL), and then heptane (626 mL) is added. The solution is stirred for 0.5-1 h and filtered over silica gel, rinsing with a mixture of ethyl acetate (351 mL) and heptane (348 mL). The solution is concentrated under reduced pressure below 45° C. and ethyl acetate (156 mL) is added. Activated carbon (3.5 g) is added and the mixture heated to 60-70° C. with stirring for 0.5-1 h. The mixture is cooled to 20-30° C., filtered, and the filtrate concentrated under reduced pressure below 45° C. Toluene (242 mL) is charged to the resulting residue and the material concentrated under reduced pressure below 45° C. Toluene (40 mL) is added and the mixture heated to 60-70° C. with stirring for 0.5-1 h. The mixture is cooled to 25-30° C., stirred for 2-4 h, and then cooled to 0-5° C. The mixture is stirred at 0-5° C. for 2-4 h and the solids are collected by filtration. The filter-cake is washed with toluene (40 mL) and is dried under reduced pressure below 60° C. to give the title compound as an off-white solid (33.0 g, 71%).

EXAMPLE 1

2-[5-(2,4-Difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol

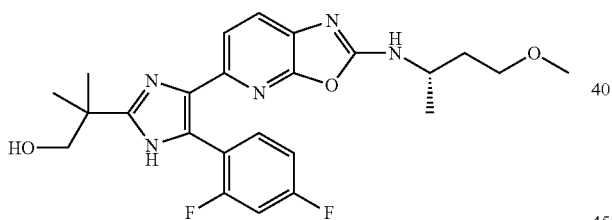

Methyl 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propanoate (497 mg, 0.99 mmol) is dissolved in a mixture of diethyl ether (5 mL) and THF (2.5 mL). The mixture is cooled to 0° C. and lithium borohydride (45.6 mg, 1.99 mmol) is added portionwise. The reaction mixture is then stirred at RT under a nitrogen atmosphere for 2 h. 1 M HCl is slowly added until pH=1 and the mixture stirred for 15 min at RT. The mixture is basified with solid NaHCO₃ and the layers are separated. The aqueous layer is extracted with dichloromethane and the combined organic layers are dried over MgSO₄, filtered, and concentrated under reduced pressure. The crude material is purified by normal phase chromatography (40 g silica-gel cartridge, 20% ethanol in hexanes). A brown solid (298 mg) is obtained, which is further purified by reverse phase chromatography (XBRIDGE™ column (5 µm, 19×100 mm): gradient between 35 and 38% of acetonitrile in ammonium carbonate solution in water (pH=9). Flow 25 mL/min) to afford 193 mg (41%) of the title compound. LC-ES/MS m/z 472 (M+1). $[\alpha]_D^{22}$+ 33.79° (c=0.72, methanol).

EXAMPLE 1

Alternate Purification

2-[5-(2,4-Difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol Methyl 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propanoate (50 g, 100.1 mmol) is dissolved in a mixture of diethyl ether (1 L) and THF (500 mL). The mixture is cooled to 0° C. and lithium borohydride (4.36 g, 200.19 mmol) is added. The reaction mixture is stirred at RT under a nitrogen atmosphere for 2 h. 1 M HCl (600 mL) is slowly added (gas evolution) and the resulting mixture is stirred for 1.5 h at RT. The layers are separated and the aqueous phase is extracted with methyl tert-butyl ether. The aqueous layer is basified (pH=8) by the addition of 2 M NaOH (200 mL) and is extracted with dichloromethane (3×400 mL). The combined organic layers are dried over Na₂SO₄, filtered, and concentrated under reduced pressure to a brown foam. The crude is eluted through a silica gel column (eluent: dichloromethane/3N NH₃ in methanol 95:5) to obtain the desired product as a violet colored foam (35 g). The solid is suspended in a mixture of 2:1 heptane/methyl tert-butyl ether and sonicated. The suspension is stirred at RT overnight. The solid is filtered and dried under a vacuum to afford the title compound as a crystalline off-white solid (30 g, 64%). MS (m/z): 472 (M+1).

EXAMPLE 1

Alternate Route of Preparations 33-41

2-[5-(2,4-Difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol

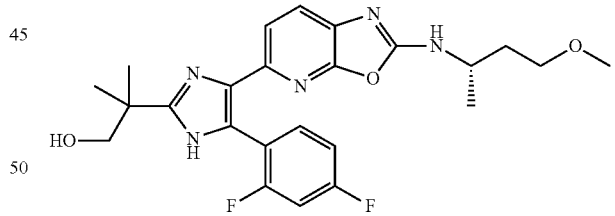

2-Methyltetrahydrofuran (135 mL) is cooled to −5 to 0° C. under nitrogen and lithium borohydride (4.95 g, 0.23 mol) is added in portions, maintaining the temperature below 10° C. A solution of methyl 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propanoate (45.0 g, 0.09 mol) in 2-methyltetrahydrofuran (225 mL) is added dropwise at −5 to 0° C. and stirred for 12-14 h. 2 M Aqueous hydrochloric acid (203 mL) is added dropwise at −5 to 0° C. and the reaction mixture is heated to 30-40° C. with stirring for 1-2 h. The reaction mixture is cooled to 15-25° C. and the layers are separated. The organic phase is extracted with a mixture of water (135 mL) and 2 M aqueous hydrochloric acid (45 mL), and the organic phase is discarded. The aqueous layers are combined and 25% aqueous sodium hydroxide (75 mL) is added dropwise to adjust to pH=8-9. The aqueous is extracted with dichloromethane (225 mL) at RT and the layers separated. The organic portion is washed with water (2×180 mL) and then concentrated under reduced pressure below 40° C. Methyl tert-butyl ether (231 mL) is added and the solution is concentrated under reduced pressure below 40° C., twice. Ethyl acetate (101 mL) is added and the mixture is heated to 50-60° C. with stirring for 1-2 h. The solution is cooled to 0-5° C. with stirring for 2-4 h. The solids are filtered and the filtercake is washed with heptane (66 mL). The solids are transferred to a reaction vessel, ethyl acetate (181 mL) is added and then the mixture is heated to 70-75° C. with stirring for 0.5-1 h. The mixture is cooled to 50-60° C. and heptane (157 mL) is added dropwise and stirred for 2-4 h. The mixture is then cooled to 10-15° C. with stirring for 2-4 h. The solids are filtered and the filtercake is washed with heptane (66 mL). The solids are transferred to a reaction vessel and ethyl acetate (406 mL) is added. The mixture is heated to 60-75° C. with stirring for 0.5-1 h. It is then cooled to 40-45° C. and is concentrate under reduced pressure below 45° C. to arrive at a solution of approximately 200 mL total volume. The mixture is heated to 70-75° C. with stirring for 0.5-1 h, and then cooled back down to 50-60° C. Heptane (268 mL) is added followed by seed crystals (2.25 g). (Seed crystals can be generated from the solids obtained from previous lots of the product of Example 1, or can be obtained using other methods common to one skilled in the art, such as recrystallization of a small aliquot.) The mixture stirred at 50-60° C. for 2-4 h. The mixture is cooled to 10-15° C. and stirred for 2-4 h. The solids are collected by filtration and the filtercake is washed with a mixture of ethyl acetate (18 mL) and heptanes (16 mL). The cake is dried under reduced pressure below 65° C. to obtain the title compound as an off-white solid (27.5 g, 63%). HPLC Method: Column. ChiralPak® AD-H, 5 μm, 4.6×250 mm; Elution mode: Isocratic; Mobile phase: Hexane/isopropanol/diethylamine (92:8:0.1); Flow rate: 1.0 mL/min; UV detection: 337 nm. $T_R$=22.6 min, 100% ee.

The Compound of Example 1, X-Ray Powder Diffraction (XRPD)

The XRPD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction pattern, collected at ambient temperature and relative humidity, is adjusted based on NIST 675 standard peaks at 8.853 and 26.774 degrees 2-theta.

TABLE 1

X-ray powder diffraction peaks of Example 1 Form I

| Peak | Angle (° 2-Theta) +/− 0.2° | Relative Intensity (% of most intense peak) | d value (angstroms) |
|---|---|---|---|
| 1 | 15.06 | 100 | 5.88 |
| 2 | 19.94 | 85.5 | 4.45 |
| 3 | 10.31 | 60.8 | 8.57 |
| 4 | 20.78 | 60.4 | 4.27 |
| 5 | 17.91 | 59.9 | 4.95 |
| 6 | 19.25 | 40.1 | 4.61 |
| 7 | 16.16 | 39.3 | 5.48 |
| 8 | 9.33 | 35.7 | 9.47 |
| 9 | 21.86 | 31.5 | 4.06 |
| 10 | 26.61 | 27.7 | 3.35 |

Thus, crystalline 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol Form I of the present invention may be characterized by an X-ray diffraction pattern using $CuK_\alpha$ radiation as having diffraction peaks (2-theta values) as described in Table 1, and in particular having peaks at 15.06 in combination with one or more of the peaks at 19.94, 10.31, and 20.78; and more particularly having a peak at 15.06; with a tolerance for the diffraction angles of 0.2 degrees.

EXAMPLE 1

Free Base Form II

The free base Form II of Example 1 is prepared by mixing 8.01 g of free base in a 125 mL flask with 100 mL of methyl tert-butyl ether to give a brown slurry of solid. The sample is slurried overnight at 300 rpm and 50° C. After 18 hours, the sample is a slurry of off-white solid under a wine-red supernatant. The sample is evaporated to reduce the volume by approximately half, and the off-white solid is recovered by vacuum filtration. The resulting cake of off-white solid is dried for 2 hours in a 65° C. vacuum oven. 7.15 g of solid is recovered (89%).

TABLE 2

X-ray powder diffraction peaks of Example 1 Form II

| Peak | Angle (° 2-Theta) +/− 0.2° | Relative Intensity (% of most intense peak) | d value (angstroms) |
|---|---|---|---|
| 1 | 13.73 | 100 | 6.45 |
| 2 | 16.54 | 67.6 | 5.35 |
| 3 | 22.87 | 66.5 | 3.89 |
| 4 | 18.57 | 62.2 | 4.77 |
| 5 | 20.80 | 37.4 | 4.27 |
| 6 | 17.47 | 37.2 | 5.07 |
| 7 | 15.30 | 34.3 | 5.79 |
| 8 | 12.36 | 31.2 | 7.16 |
| 9 | 12.87 | 29.4 | 6.87 |
| 10 | 9.61 | 22.3 | 9.20 |

Thus, crystalline 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol Form II of the present invention may be characterized by an X-ray diffraction pattern using $CuK_\alpha$ radiation as having diffraction peaks (2-theta values) as described in Table 1, and in particular having peaks at 13.73 in combination with one or more of the peaks at 16.54, 22.87, and 18.57; and more particularly having a peak at 13.73; with a tolerance for the diffraction angles of 0.2 degrees.

EXAMPLE 2

2-[5-(2,4-Difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol, methanesulfonate 2-[5-(2,4-Difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol (37.5 mg, 0.080 mmol) is dissolved in a 1:1 mixture of dichloromethane/methanol (1 mL total). A 0.5 M solution of methanesulphonic acid in methanol (0.16 mL) is added dropwise. The mixture is stirred at RT for 30 min. The solvent is evaporated under reduced pressure and the resulting residue is triturated twice with tert-butyl methyl ether. The residue is dried under vacuum to afford the title compound (42 mg, 93%). LC-ES/MS m/z 472 (M+1).

EXAMPLE 3

2-[5-(2,4-Difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol, hydrochloride To a slightly pink suspension of 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol (25.7 g, 54.51 mmol) in methyl tert-butyl ether (771 mL) at 60° C., is added a 4.0 M HCl solution in dioxane (16.35 mL, 65.41 mmol). The resulting suspension is heated to 60° C. for 30 min and then allowed to reach RT gradually. A solid is formed and is filtered under an inert atmosphere of nitrogen and quickly collected and dried under vacuum at 60° C. overnight to provide the title compound as a creamy solid (27 g, 98%). LC-ES/MS m/z 472 (M+1).

EXAMPLE 4

2-[5-(2,4-Difluorophenyl)-4-[2-[[(1R)-3-methoxy-1-methyl-propyl]amino]oxazolo[5,4-b]pyridin-5-yl]-1H-imidazol-2-yl]-2-methyl-propan-1-ol

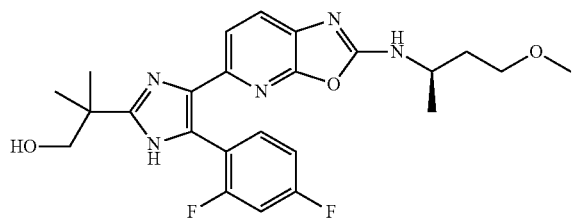

The title compound is prepared essentially using the same synthetic route as for its S enantiomer, with the difference that, in Preparation 1, (1R)—N-benzyl-1-phenyl-ethanamine is used instead of the S enantiomer. $[\alpha]_D^{22}$ −32.11°, (c=0.54, methanol).

EXAMPLE 5

2-[5-(2,4-Difluorophenyl)-4-[2-[[(1R)-3-methoxy-1-methyl-propyl]amino]oxazolo[5,4-b]pyridin-5-yl]-1H-imidazol-2-yl]-2-methyl-propan-1-ol methanesulfonate The title compound is prepared using essentially the same procedure as described in Example 2 for its S enantiomer.

EXAMPLE 6

5-[2-Cyclopropyl-5-(2,4-difluorophenyl)-1H-imidazol-4-yl]-N-[(1S)-3-methoxy-1-methyl-propyl]oxazolo[5,4-b]pyridin-2-amine

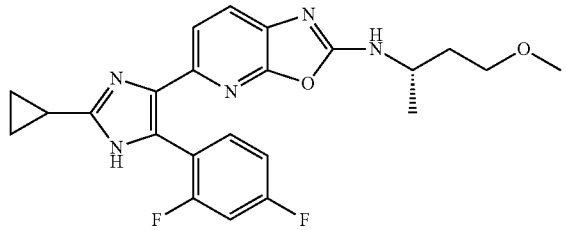

A KIMAX® tube is charged with 3-amino-6-[2-cyclopropyl-5-(2,4-difluorophenyl)-1H-imidazol-4-yl]pyridin-2-ol (0.7 g, 2.13 mmol) and ethanol (7 mL). (3S)-3-isothiocyanato-1-methoxy-butane (0.46 g, 3.2 mmol) is added, the flask sealed, and the mixture is heated to 85° C. After 16 h, N,N'-dicyclohexylcarbodiimide (0.88 g, 4.26 mmol) is added and the mixture is stirred for 4 h at 85° C. in the sealed tube. After this time, additional N,N'-dicyclohexylcarbodiimide (0.44 g, 2.13 mmol) is added to the mixture. Heating is continued at 85° C. overnight. After this time, additional N,N'-dicyclohexyl-carbodiimide (0.88 g, 4.26 mmol) is added to the mixture, and heating is continued at 85° C. for 4 h. The crude reaction is concentrated under reduced pressure, and the residue is purified by normal phase chromatography (120 g silica-gel cartridge, dichloromethane-ethanol gradient). The fractions containing the desired compound are further purified by semi-preparative reverse phase high performance (LC/MS) using an XBRIDGE™ column (5 μm, 19×100 mm) and an isocratic program of 36% of acetonitrile in $NH_4HCO_3$ 20 mM (pH 9), in 5 min at flow 25 mL/min to afford the title compound (0.15 g, 16%). LCES/MS m/z 440 (M+1); $[\alpha]_D^{22}$+ 58.60°, (c=0.50, methanol).

EXAMPLE 7

5-[2-Cyclopropyl-5-(2,4-difluorophenyl)-1H-imidazol-4-yl]-N-[(1S)-3-methoxy-1-methyl-propyl]oxazolo[5,4-b]pyridin-2-amine methanesulfonate 5-[2-Cyclopropyl-5-(2,4-difluorophenyl)-1H-imidazol-4-yl]-N-[(1S)-3-methoxy-1-methyl-propyl]oxazolo[5,4-b]pyridin-2-amine (0.090 g, 0.23 mmol) is dissolved in a 1:1

EXAMPLE 8

5-[5-(2,4-Difluorophenyl)-2-(3-methyloxetan-3-yl)-1H-imidazol-4-yl]-N-[(1S)-3-methoxy-1-methyl-propyl]oxazolo[5,4-b]pyridin-2-amine

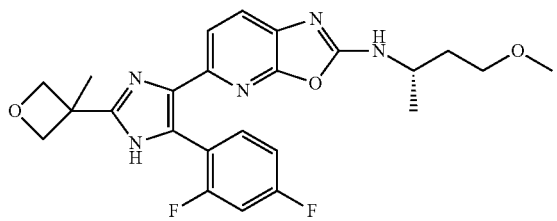

mixture of dichloromethane and methanol (3 mL total). A 0.5 M solution of methanesulfonic acid in methanol (0.47 mL) is added dropwise to the solution. The mixture is stirred at RT for 30 min and then the solvent is evaporated under reduced pressure. The residue is mixed with methanol and concentrated twice to afford the title compound (0.111 g, 89%). LC-ES/MS m/z 440 (M+1).

A KIMAX® tube is charged with 3-amino-6-[5-(2,4-difluorophenyl)-2-(3-methyloxetan-3-yl)-1H-imidazol-4-yl]pyridin-2-ol (2.28 g, 6.36 mmol) and ethanol (18 mL). (3S)-3-Isothiocyanato-1-methoxy-butane (1.39 g, 9.54 mmol) is added, the flask sealed, and the mixture is heated to 85° C. After 16 h, (3S)-3-isothiocyanato-1-methoxy-butane (700 mg) is added and the mixture is stirred for 48 h at 85° C. in the sealed tube. N,N'-diisopropylcarbodiimide (1.04 g) is added and the mixture is stirred 3 h at 85° C. in the sealed tube. The crude reaction mixture is concentrated under reduced pressure and the residue purified by normal phase chromatography (120 g silica-gel cartridge, hexane-ethanol). The desired compound elutes at 3% of ethanol to give the title compound as a brown solid (2.61 g, 87%). LC-ES/MS m/z 470 (M+1); $[\alpha]_D^{22}$+42.2°, (c=0.50, methanol).

EXAMPLE 9

5-[5-(2,4-Difluorophenyl)-2-(3-methyloxetan-3-yl)-1H-imidazol-4-yl]-N-[(1S)-3-methoxy-1-methyl-propyl]oxazolo[5,4-b]pyridin-2-amine methanesulfonate 5-[5-(2,4-Difluorophenyl)-2-(3-methyloxetan-3-yl)-1H-imidazol-4-yl]-N-[(1S)-3-methoxy-1-methyl-propyl]oxazolo[5,4-b]pyridin-2-amine (0.72 g, 1.54 mmol) is dissolved in a 1:1 mixture of dichloromethane/methanol (15 mL total). A 0.5 M solution of methanesulfonic acid in methanol (3.07 mL) is added dropwise to the solution. The mixture is stirred at RT for 30 min and then the solvent is evaporated under reduced pressure. The residue is triturated with tert-butyl methyl ether to afford the title compound as a brown solid (0.841 g, 97%). LC-ES/MS m/z 470 (M+1).

EXAMPLE 10

[1-[5-(2,4-Difluorophenyl)-4-[2-[[(1S)-2-ethoxy-1-methyl-ethyl]amino]oxazolo[5,4-b]pyridin-5-yl]-1H-imidazol-2-yl]cyclopropyl]methanol

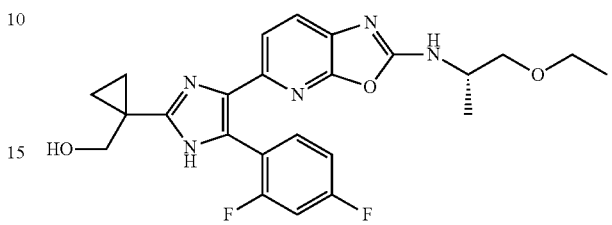

Methyl 1-[5-(2,4-difluorophenyl)-4-[2-[[(1S)-2-ethoxy-1-methyl-ethyl]amino]oxazolo[5,4-b]pyridin-5-yl]-1H-imidazol-2-yl]cyclopropanecarboxylate (0.9 g, 1.99 mmol) is dissolved in dry diethyl ether (20 mL) and dry THF (7 mL) under a nitrogen atmosphere and cooled to 0° C. Lithium borohydride (87 mg, 3.99 mmol) is added portionwise and the mixture stirred at 0° C. for 1 h. The remaining reactants are quenched by adding 1 N HCl until pH=1 to the mixture at RT dropwise for 30 min. The mixture is washed with ethyl acetate, the aqueous layer basified (until pH=8) with NaOH, and extracted with dichloromethane. The combined organic layers are dried over MgSO₄, filtered, and concentrated under reduced pressure. The residue is purified by normal phase chromatography (120 g silica-gel cartridge) using a gradient of hexane-ethanol to afford the title compound (0.56 g, 60%). LC-ES/MS m/z 470.2 (M+1); $[\alpha]_D^{22}$−18.00°, (c=0.50, MeOH); $[\alpha]_D^{22}$−18.0°, (c=0.50, CHCl₃).

EXAMPLE 11

[1-[5-(2,4-Difluorophenyl)-4-[2-[[(1S)-2-ethoxy-1-methyl-ethyl]amino]oxazolo[5,4-b]pyridin-5-yl]-1H-imidazol-2-yl]cyclopropyl]methanol methanesulfonate

[1-[5-(2,4-Difluorophenyl)-4-[2-[[(1S)-2-ethoxy-1-methyl-ethyl]amino]oxazolo[5,4-b]pyridin-5-yl]-1H-imidazol-2-yl]cyclopropyl]methanol (0.56 g, 1.19 mmol) is dissolved in a 1:1 mixture of dichloromethane/methanol (12 mL total). A 0.5 M solution of methanesulfonic acid in methanol (2.37 mL) is added dropwise to the solution. The mixture is stirred at RT for 30 min and then the solvent is evaporated under reduced pressure. The residue is mixed with methanol and concentrated twice to afford the title compound (0.64 g, 96%). LC-ES/MS m/z 470.1 (M+1).

Biological Assays

The following assays demonstrate that the exemplified compounds of the present invention are potent inhibitors of p38α MAP kinase, are potent inhibitors of p38β MAP kinase, and are potent inhibitors of p38 MAP kinase signaling in cancer cells. The following assays also demonstrate that Example 1 or salts of Example 1 (Examples 2 or 3) have potent activity in vivo, and are effective anticancer agents either alone and/or in combination with other oncolytic agents.

Inhibition of p38α MAP Kinase Enzyme Activity

Reagent Preparation:

The kinase reaction buffer is prepared as a stock solution containing 1440 µL of 1 M 4-(2-hydroxyethyl)-1-piperazineethanesulfonic acid (HEPES) pH 7.5, 240 µL of 1 M $MgCl_2$, 72 µL of 1 M dithiothreitol (DTT), 25 µL of 10% TRITON® X-100, 43223 µL of $H_2O$. The substrate mix is prepared by combining the following: 2775 µL kinase reaction buffer, 75.0 µL adenosine triphosphate (ATP) at 10 mM, 270 µL EGFR peptide (Upstate Biotechnology/Millipore) at 4 mM (9.17 mg/mL) and 12.5 µL $^{33}$P-ATP. The p38 MAP kinase enzyme stock solution is prepared by diluting 0.1 mg/mL solution of purified human p38α MAP kinase in 3000 µL of reaction buffer. Stock solutions of test compounds are generated by dissolving the compounds in 100% dimethyl sulfoxide (DMSO) at 10 mM. 100 µM stock dilution plates are generated by diluting 2 µL of 10 mM stock in 198 µL of 20% DMSO. 1:3 dilutions in 20% DMSO are generated from the 100 µM stock using a Tecan liquid handler.

Kinase Assay:

For the kinase assay, 5 µL of diluted compound is transferred to the reaction plate, followed by 10 µL of enzyme stock solution (added using a MULTIDROP® liquid dispenser). To start the reaction, 10 µL of substrate mix is added with a MULTIDROP® and the plate is shaken for 30 seconds. Final reaction conditions are as follows: 25 mM HEPES pH 7.5, 4.25 mM $MgCl_2$, 1.30 mM DTT, 0.004% TRITON® X-100, 100 µM ATP, 100 µM EGFR peptide, 11.8 nM p38α MAP kinase, and 4% DMSO. The reaction is incubated at RT for 60 minutes and then stopped by addition of 75 µL of 5% acetic acid (freshly prepared). After stopping, 100 µL of the reaction mixture is transferred to a phosphocellulose filter plate (Millipore, NAPH) that is pre-washed with 100 µL of 0.5% acetic acid. The reaction mixture is incubated on the phosphocellulose plate for 30 minutes, filtered using a vacuum manifold, and washed once with 300 µL and then twice with 200 µL of 0.5% orthophosphoric acid. Following the washing steps, 80 µL of MICROSCINT™20 is added and the radioactivity counted in a Trilux MICROBETA®. $IC_{50}$ values are calculated using Activity Base software (IDBS). All exemplified compounds have an $IC_{50}$ of less than 0.050 µM. For example, Example 1 has an $IC_{50}$=0.003 µM. This assay demonstrates that the compound of Example 1 is a potent inhibitor of p38α MAP kinase.

Inhibition of p38β MAP Kinase Enzyme Activity

Reagent Preparation:

The kinase reaction buffer is prepared essentially as described above. The substrate mix is prepared by combining the following: 2840 µL Kinase Reaction Buffer, 15.0 µL ATP at 10 mM, 125 µL EGFR peptide at 4 mM (9.174 mg/ml), 18.75 µL $^{33}$P-ATP. The p38β MAP kinase enzyme stock solution is prepared by diluting 2.25 µL of a 0.57 mg/mL solution of commercial p38β MAP kinase (Upstate Biotechnology/Millipore) in 2000 µL of reaction buffer. Stock solutions of test compounds are generated essentially as described above.

Kinase Assay:

The kinase assay is performed essentially as described for p38α MAP kinase. Final reaction conditions are as follows: 25 mM HEPES pH 7.5, 4.25 mM $MgCl_2$, 1.30 mM DTT, 0.004% TRITON® X-100, 20 µM ATP, 65 µM EGFR peptide, 0.25 ng/µL p38β MAP kinase, 4% DMSO. All exemplified compounds have an $IC_{50}$ of less than 0.050 µM. For example, Example 1 has an $IC_{50}$=0.007 µM. This assay demonstrates that the compound of Example 1 is a potent inhibitor of p38β MAP kinase.

Inhibition of p38 MAP Kinase in the Cell-Based Assay p38 MAP kinase inhibition in HeLa cells is assayed by measuring p-MAPKAPK2 levels following TNFα stimulation in the presence of test compound. Human HeLa cells (ATCC) are cultured in Dulbecco's Modification of Eagle's Medium (DMEM media) containing 10% fetal bovine serum (FBS, GIBCO). Test compounds are prepared in 1:3 dilution series in cell culture media with a final DMSO concentration of 0.1%. For the assay, 60,000 cells per well are plated in 100 µL of DMEM media containing 10% fetal bovine serum in a 96 well poly-D-lysine plate. Cells are incubated overnight at 37° C. in a 5% $CO_2$ incubator. The next day, plates are inverted to dispose of media and 90 µL of fresh media containing either DMSO (control wells) or the test compound dilution series is added. Plates are incubated for 1 hour at 37° C. in the presence of 5% $CO_2$. After 1 hour, 20 µL of a 100 ng/mL solution of human TNFα (made in DMEM/FBS) is added to the wells, to give a final concentration of 18.2 ng/mL. All wells are treated with TNFα, except the control minimum signal wells, which do not receive TNFα. Cells are incubated with the TNFα for 15 minutes (37° C./5% $CO_2$) in order to stimulate phosphorylation of MAPKAPK-2, the p38 MAP kinase substrate.

For the cELISA assay, media is removed by inverting the plate. Cells are fixed by addition of PREFER® fixative (Anatech Ltd) for 30 minutes at RT. Cells are washed three times for 5 minutes each time with 100 µL of phosphate buffered saline (PBS) containing 0.1% TRITON® X-100 (this mixture is identified as PBST). 100 µL of 0.6% $H_2O_2$ in PBST is added to the cells for 15 minutes to quench the peroxidase, followed again by washing three times for 5 minutes each time with PBST. Cells are blocked by addition of a 5% bovine serum albumin (BSA) solution at RT for 1 hour. Cells are washed three times for 5 minutes each time with PBST. Cells are incubated with a 1/1000 dilution of primary antibody directed against p-MAPKAPK-2 Thr334 (Cell Signaling) in PBST containing 5% BSA at 4° C. overnight. Cells are washed three times for 5 minutes each time with PBST. Cells are treated with the secondary antibody, peroxidase-conjugated anti-rabbit Ig antibody (Amersham), at 1/1000 dilution in PBST with 5% BSA for 1 hour at RT. Cells are washed three times for 5 minutes each time with PBST.

For detection of signal, a SUPERSIGNAL® ELISA femto kit (Pierce) is used. Equal parts of Femto luminal/enhancer and peroxidase are mixed prior to use. 100 µL of the mixture is added to each well and shaken for 1 minute using a microplate mixer. Relative light units are determined using a Victor 1420 luminometer. Relative $IC_{50}$ values are determined using Activity Base software (IDBS). All exemplified compounds have an $IC_{50}$ of less than 0.050 µM. For example, Example 1 has an $IC_{50}$=0.0016 µM. This assay demonstrates that the compound of Example 1 is a potent inhibitor of p38 MAP kinase signaling in cancer cells.

In Vivo Target Inhibition (IVTI) of p38 MAP Kinase in Naïve C57BL/6 Mice

IVTI of p38 MAP kinase is measured in peripheral blood mononuclear cells (PBMCs) of mice dosed orally with test compound using a flow cytometry assay for p-MAPKAPK2, a p38 MAP kinase substrate.
Live Phase:
Male C57BL/6 mice (6-8 weeks old) are randomized into groups of 4. Test compound is administered by oral gavage in a 0.1 mL volume of vehicle (1% hydroxyethyl cellulose (HEC), 0.25% TWEEN® 80, 0.05% antifoam). Control animals are administered 0.1 mL vehicle with no test compound. For single dose and dose response studies, animals are sacrificed 2 hour post-dose. For time-course studies, animals are sacrificed at different time-points post-dose, typically, 1, 2, 4, 6, 18 and 24 hours. Whole blood is collected in EDTA-coated tubes (AQUISEL).
Phospho-MAPKAPK2 Detection in PBMCs by Flow Cytometry:
100 µL mouse whole blood is added into each EDTA tube and incubated at 37° C. for 10 minutes. A mixture of three antibodies are prepared at the following dilutions in stain/wash buffer: FITC-conjugated rat anti-mouse Ly-6G mAb (BD Biosciences) 1:25; APC-conjugated rat anti-mouse CD11b mAb (BD Biosciences) 1:10; and Mouse BD Fc Block (BD Biosciences) 1:100. A stock solution of anisomycin (Sigma) is made at a concentration of 5 mg/mL in DMSO. 15 µL of stock anisomycin is aliquoted in single tubes and stored at −20° C. for single usage. On the day of the assay, the anisomycin is diluted from stock (5 mg/mL) to 100 µg/mL in stain/wash buffer (BD). An equal volume of diluted anisomycin is mixed with the antibody mixture.
20 µL of the mixture above is added into each whole blood tube, one tube every 20 sec. The sample is incubated at 37° C. for 15 minutes in a thermomixer with gentle shaking. Lyse/Fix buffer (BD Biosciences) is diluted 5× in water and warmed to 37° C. 1.6 mL of the diluted Lyse/Fix buffer (=1× working concentration) is added into each tube, one tube every 20 sec, in the same sequence as previously. Samples are incubated at 37° C. for 10 minutes with shaking. Cells are then spun down at 600×g, for 8 minutes at RT. Cells are washed once with 3 mL wash/stain buffer, PBS and 5% decomplemented (heat-inactivated) FBS. The supernatant is discarded carefully to avoid losing cell pellets. Anti-Phospho-MAPKAPK-2 (Thr334) antibody (Cell Signaling Technology, clone 27B) and mouse Fc block are diluted together in Permeabilization Medium B (Caltag) (250× dilution for both). 200 µL of diluted antibody mix is used to re-suspend the cells.
Cells are then incubated at RT for 30 minutes. 3 mL of Stain/wash buffer is then added and cells spun down as described above. The wash is repeated with 3 mL of stain/wash buffer. Goat F(ab')2 anti-rabbit immunoglobulin-PE Conjugate (Biosource) is diluted in stain/wash buffer (250× dilution). 200 µL of diluted antibody is then added into each tube.
Samples are incubated at RT for 30 minutes. 3 mL of stain/wash buffer is then added and the cells are spun down. The wash is repeated with 3 mL of stain/wash buffer. Finally, cells are re-suspended in 250 µL PBS plus 1% of decomplemented (heat-inactivated) FBS. Samples are analyzed by flow cytometry (FACScaliber, BD). After defining the viable single cell population by side and forward scatter, the level of p-MAPKAPK2 is measured in the monocyte population defined (gated) by CD11b$^{hi}$Ly6G$^{-}$.
Data Analysis:
The median fluorescence intensity in the monocyte cells is analyzed to determine the level of p-MAPKAPK2. The level of p-MAPKAPK2 (pMK2) in anisomycin-stimulated minus unstimulated monocytes from vehicle control animals is used to determine the signal window. Percent inhibition by test compound is determined by using the following equation:

$$\% \text{ inhibition} = 100 - \left[ 100 * \frac{\left( \begin{array}{c} \text{stimulated } pMK2 - \text{unstimulated } pMK2 \\ \text{in compound animals} \end{array} \right)}{\left( \begin{array}{c} \text{stimulated } pMK2 - \text{unstimulated } pMK2 \\ \text{in vehicle animals} \end{array} \right)} \right]$$

Using this protocol, the Threshold Efficacious Dose for 70% inhibition ($TED_{70}$) for the compound of Example 1 is 5.1 mg/kg at 2 hours post-dose. The Threshold Efficacious Concentration for 70% inhibition ($TEC_{70}$) determined by measuring circulating compound in plasma in the same assay is 39.4 ng/mL (0.084 µM) at 2 hours post-dose. This assay demonstrates that the compound of Example 1 has potent activity in vivo.

In Vivo Inhibition of p38 MAP Kinase in Tumor-Bearing Mice

A murine xenograft model utilizing the human tumor cell line, U87MG, is used for assessment of inhibition of p38 MAP kinase in tumors
Live Phase:
Female athymic nude mice (24-26 g, Harlan) are injected subcutaneously in the rear flank with 5×10$^6$ U87MG cells per animal Cells are injected in a 0.2 mL volume with a 1:1 mixture of cell culture media and BD MATRIGEL™ matrix. 7 days after implant tumors are measured using a caliper and the data recorded. Tumors are measured twice weekly thereafter and the tumor size is recorded. When tumors reach an average volume of approximately 250 mm³ (usually 10-15 days after implant), animals are randomized into groups of 8-10 for treatment. Animals are then dosed orally with 0.2 mL vehicle (1% HEC, 0.25% TWEEN® 80, 0.05% antifoam) alone or vehicle containing test compound. 2 Hours after dosing, animals are euthanized. The tumors are excised and processed immediately by homogenization in a solution of 1% TRITON® X-100 with a cocktail of complete protease and phosphatase inhibitors (Roche Standard tablets complete, EDTA-free Protease Inhibitor Cocktail. cat#11873580001). In addition, blood is collected in ethylenediaminetetraacetic acid (EDTA)-coated tubes and plasma generated in a 96 well plate format for exposure analysis.

p-MAPKAPK2 Assay in Tumor Lysates:

p-MAPKAPK2 levels in the tumor lysates are determined using a Mesoscale Discovery (MSD) capture ELISA kit (2 Phospho-MAPKAPK-2 (Thr334)). The concentration of protein in the lysates is determined using a BioRad DC protein assay kit (BioRad). Protein samples from each tumor lysate are adjusted to 2 mg/mL using a solution of 1% TRITON® X-100. For mesoscale detection of p-MAPKAPK2, 50 µg of tumor lysate is added to a carbon electrode-containing 96-well plate pre-spotted with the capture antibody (=antibody against total MAPKAPK2 protein). The p-MAPKAPK2 level is probed using a ruthenium-labeled anti p-MAPKAPK2 detection antibody. Following incubation with the detection antibody, the MSD plate is washed followed by addition of MSD read buffer. After passage of current over the electrode, electro-chemiluminescence results in the generation of light that is quantified using the MSD Sector 6000 instrument. For each study, percent inhibition is calculated relative to the vehicle control group, and ANOVA (means of calculating statistical analysis of variance) analysis performed using the JMP software package for the determination of statistical significance. The analysis is confirmed by immunoblots in representative studies. From this study, it is determined that the compound of Example 1 has a $TED_{70}$ for p38 MAP kinase target inhibition in tumors of 2.9 mg/kg, and the $TEC_{70}$ is 31.3 ng/mL. This data demonstrates that, for the compound of Example 1, target inhibition potency is similar in the tumor as in the PBMCs.

Determination of In Vivo Efficacy in Xenograft Models

A2780 Xenograft Model:

Female CD1 nu/nu mice are obtained from Charles River Laboratories at approximately 22-25 g. After 1 week acclimation, 2×10⁶ A2780 human ovarian carcinoma cells are injected subcutaneously in the rear flank of each mouse in a 0.2 mL volume in a 1:1 mixture of cell culture media and BD MATRIGEL™ matrix. Tumor size is monitored by caliper measurement twice per week. When the average tumor size reaches 150 mm³, animals are randomized into groups of 10. p38 MAP kinase inhibitor treatment is initiated after randomization. Example 2 is dosed orally in a 0.2 mL volume of 1% HEC, 0.25% TWEEN® 80, 0.05% antifoam (HEC/TWEEN®). The compound is dosed at doses of 1, 3, and 10 mg/kg. Dosing is performed three times per day (TID) on a schedule of 4 days on, 3 days off. Three cycles of dosing is performed. Tumor volume is monitored twice per week during the dosing period, and efficacy (tumor growth inhibition) is monitored relative to a vehicle control group (n=10 animals). At 1, 2 and 8 hours after the last p38 MAP kinase inhibitor dose, plasma is obtained from animals to determine the circulating levels of compound in the animals.

| Treatment Groups (PO, TID, 4 day on, 3 d off, 4 cycles) | Tumor Growth Inhibition (%) | | | | Mean Plasma Concentration (µM) at time (hour) post-last dose | | |
|---|---|---|---|---|---|---|---|
| | Day | Day | Day | Day | | | |
| (mg/kg) | 20 | 23 | 26 | 29(final) | 1 | 2 | 3 |
| 1 | 70.6 | 76.6 | 76 | 78.3 | 0.0263 | 0.0146 | BQL < (1.00) |
| 3 | 32.5 | 47.7 | 42.7 | 37.7 | 0.0526 | 0.0604 | 0.0042 |
| 10 | 60 | 71.2 | 72.8 | 74.8 | 0.4952 | 0.3978 | 0.0243 |

OPM-2 Multiple Myeloma Xenograft Model:

Female CB-17 SCID mice are obtained from Taconic at 20-22 g weight. After acclimating for one week, mice are irradiated with a dose of 2.5 Gray. Within 24 hours following irradiation, mice are injected sub-cutaneously in the rear flank with 1.0×10⁷ OPM-2 cells in a 0.2 mL volume in a 1:1 mixture of cell culture media and BD MATRIGEL™ matrix. Tumor size is monitored by caliper measurement twice per week. When the tumor size reaches 100-150 mm³, animals are randomized into dose groups. Compound treatment is initiated after randomization. Example 2 is dosed orally in a 0.2 mL volume of 1% HEC, 0.25% TWEEN® 80, 0.05% antifoam (HEC/TWEEN®). The compound is dosed at doses of 15 and 30 mg/kg. Dosing is performed two times per day (BID) for 28 days of treatment. Tumor volume is monitored twice per week during the dosing period, and efficacy (tumor growth inhibition) is monitored relative to a vehicle control group (n=10 animals).

| | Group Name: | | | | | | | | | |
|---|---|---|---|---|---|---|---|---|---|---|
| | HEC/TWEEN, 0.2 ml, PO, BID | | | | Example 2, 15 mpk, PO, BID | | | Example 2, 30 mpk, PO, BID | | |
| Day | no. mice | Mean tumor size (mm3) | SE | Signif. | no. mice | Mean tumor size (mm3) | SE | Signif. | no. mice | Mean tumor size (mm3) | SE | Signif. |
| 4 | 10 | 102.8 | 20.84 | Ctrl | 9 | 101.69 | 18.94 | NS | 9 | 97.8 | 16.77 | NS |
| 8 | 10 | 88.54 | 17.95 | Ctrl | 9 | 87.96 | 16.38 | NS | 9 | 90.78 | 15.57 | NS |
| 11 | 10 | 141.58 | 28.7 | Ctrl | 9 | 104.9 | 19.54 | NS | 9 | 118.46 | 20.32 | NS |
| 15 | 10 | 132.95 | 26.95 | Ctrl | 8 | 104.21 | 19.65 | NS | 9 | 95.34 | 16.35 | NS |
| 18 | 10 | 161.01 | 32.64 | Ctrl | 8 | 120.17 | 22.83 | NS | 9 | 103.71 | 17.79 | * |
| 21 | 10 | 211.27 | 42.83 | Ctrl | 8 | 182.47 | 34.89 | NS | 9 | 115.16 | 19.75 | ** |
| 25 | 10 | 233.07 | 47.25 | Ctrl | 8 | 169.53 | 32.63 | NS | 9 | 155.27 | 26.63 | NS |
| 29 | 10 | 289.92 | 58.77 | Ctrl | 8 | 214.28 | 41.47 | NS | 9 | 154.83 | 26.56 | ** |
| 33 | 10 | 464.75 | 94.21 | Ctrl | 8 | 326.29 | 63.41 | NS | 9 | 224.14 | 38.45 | ** |
| 36 | 10 | 635.98 | 128.92 | Ctrl | 8 | 384.59 | 74.93 | * | 9 | 243.32 | 41.74 | *** |
| 43 | 10 | 875.15 | 177.41 | Ctrl | 8 | 628.46 | 123.01 | NS | 9 | 407.07 | 69.82 | *** |
| 46 | 9 | 1162.28 | 237.09 | Ctrl | 8 | 700.62 | 137.33 | * | 9 | 527.14 | 90.42 | *** |
| 49 | 8 | 1238.92 | 256.05 | Ctrl | 8 | 937.29 | 183.95 | NS | 9 | 642.22 | 110.16 | ** |
| 53 | 8 | 1437.56 | 301.51 | Ctrl | 8 | 1138.19 | 223.68 | NS | 9 | 812.48 | 139.37 | * |

786-O Xenograft Model in Combination with Sunitinib:

Female athymic nude mice are obtained from Harlan Labs at a weight of 24-26 g. After 1 week acclimation, 5×10$^6$ 786-O human renal cell carcinoma cells are injected subcutaneously in the rear flank of each mouse in a 0.2 mL volume in a 1:1 mixture of cell culture media and BD MATRIGEL™ matrix. Tumor size is monitored by caliper measurement twice per week. When the average tumor volume reaches 150-200 mm$^3$, animals are randomized into groups of 8-10. p38 MAP kinase inhibitor treatment is initiated after randomization. The compound is dosed orally in a 0.2 mL volume of 1% HEC, 0.25% TWEEN® 80, 0.05% antifoam (HEC/TWEEN®). Dosing is performed twice per day (BID) at 15 mg/kg either alone or in combination with 10 mg/kg or 20 mg/kg of sunitinib, also dosed orally BID in the same vehicle. Tumor volume is monitored twice per week and efficacy (tumor growth inhibition) is compared relative to vehicle-treated control animals.

The compounds of the present invention are preferably formulated as pharmaceutical compositions administered by a variety of routes. Most preferably, such compositions are for oral or intravenous administration. Such pharmaceutical compositions and processes for preparing same are well known in the art. See, e.g., REMINGTON: THE SCIENCE AND PRACTICE OF PHARMACY (D. Troy, et al., eds., 21$^{st}$ ed., Lippincott Williams & Wilkins, 2005).

The compounds of the present invention are generally effective over a wide dosage range. For example, dosages per day normally fall within the range of about 14-155 mg. In some instances dosage levels below the lower limit of the aforesaid range may be more than adequate, while in other cases still larger doses may be employed without causing any harmful side effect, and therefore the above dosage range is

| Group# | Treatment Groups (PO, BID x 28) | Number of Subjects | % Tumor Growth Inhibition | | | | |
|---|---|---|---|---|---|---|---|
| | | | Day 17 | Day 21 | Day 24 | Day 28 | Day 31 |
| 1 | HEC/TWEEN ®, 0.2 mL HEC/TWEEN ® 0.2 mL | 10 | 0 | 0 | 0 | 0 | 0 |
| 2 | Example 3 15 mg/kg HEC/TWEEN ® 0.2 mL | 8 | −35.5 | −23 | −52.4 | −74.1* | −58.8* |
| 3 | Sunitinib 10 mg/kg HEC/TWEEN ® 0.2 mL | 8 | −1.6 | 2.9 | −16.3 | −21.2 | −27.7 |
| 4 | Sunitinib 20 mg/kg HEC/TWEEN ® 0.2 mL | 8 | −55.9 | 31.5 | 18 | 34.5 | 35.4* |
| 5 | Example 3 15 mg/kg Sunitinib 10 mg/kg | 8 | −31.3 | 9.8 | −14.9 | −23.2 | −0.4 |
| 6 | Example 3 15 mg/kg Sunitinib 20 mg/kg | 8 | 69.4* | 96.8* | 89* | 99.1* | 97.5* |

*statistically significant compared to vehicle.

Data from this study demonstrates that p38 MAP kinase inhibition (15 mg/kg BID) enhances the anti-tumor efficacy of sunitinib dosed at 20 mg/kg. Statistical assessment of synergy was performed using two-way repeated measures analysis of variance on log tumor volume vs. time. This analysis demonstrated overall significant synergy (p>0.0001) between 15 mg/kg BID of the p38 MAP kinase inhibitor and 20 mg/kg BID of sunitinib.

not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula:

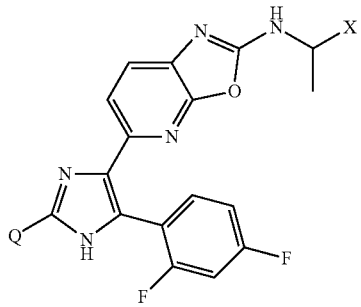

where:

X is methoxyethyl or ethoxymethyl;

Q is cyclopropyl, 2-methyl-propanol-2-yl, 3-methyloxetan-3-yl, 1-hydroxymethyl-1-cyclopropyl;

or a pharmaceutically acceptable salt thereof.

2. The compound according to claim 1 which is 2-[5-(2,4-difluorophenyl) -4-[2-[[(1S)-3-methoxy-1-methyl-propyl]amino]oxazolo[5,4-b]pyridin-5-yl]-1H-imidazol-2-yl]-2-methyl-propan-1-ol, or a pharmaceutically acceptable salt thereof.

3. The compound according to claim 2 which is crystalline 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol characterized by the X-ray powder diffraction pattern (Cu radiation, λ=1.54060 Å) comprising a peak at 15.06, and one or more peaks at 19.94, 10.31, and 20.78 (2θ+/−0.2°).

4. The compound according to claim 2 which is crystalline 2-[5-(2,4-difluorophenyl)-4-[2-[[(1S)-3-methoxy-1-methyl-propyl]amino]oxazolo[5,4-b]pyridin-5-yl]-1H-imidazol-2-yl]-2-methyl-propan-1-ol characterized by the X-ray powder diffraction pattern (Cu radiation, λ=1.54060 Å) comprising a peak at 13.73, and one or more peaks at 16.54, 22.87, and 18.57 (2θ+/−0.2°).

5. The compound according to claim 1 which is 5-[2-cyclopropyl-5-(2,4-difluorophenyl)-1H-imidazol-4-yl]-N-[(1S)-3-methoxy-1-methyl -propyl]oxazolo[5,4-b]pyridin-2-amine, or a pharmaceutically acceptable salt thereof.

6. The compound according to claim 1 which is 5-[5-(2,4-difluorophenyl) -2-(3-methyloxetan-3-yl)-1H-imidazol-4-yl]-N-[(1S)-3-methoxy-1-methyl-propyl]oxazolo[5,4-b]pyridin-2-amine, or a pharmaceutically acceptable salt.

7. The compound according to claim 1 which is [1-[5-(2,4-difluorophenyl)-4-[2-[[(1S)-2-ethoxy-1-methyl-ethyl]amino]oxazolo[5,4-b]pyridin-5-yl]-1H-imidazol-2-yl]cyclopropyl]methanol, or a pharmaceutically acceptable salt.

8. A pharmaceutical composition comprising a compound of the formula:

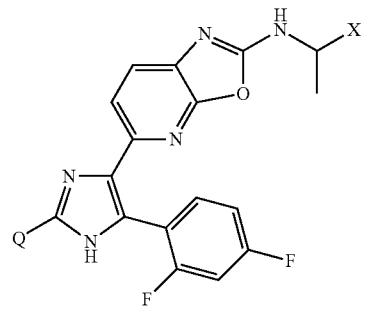

where:

X is methoxyethyl or ethoxymethyl;

Q is cyclopropyl, 2-methyl-propanol-2-yl, 3-methyloxetan-3-yl, 1-hydroxymethyl-1-cyclopropyl;

or a pharmaceutically acceptable salt thereof;

in combination with one or more pharmaceutically acceptable carriers, diluents or excipients.

9. A method of treating cancer in a mammal comprising administering to a mammal in need of such treatment an effective amount of a compound of the formula:

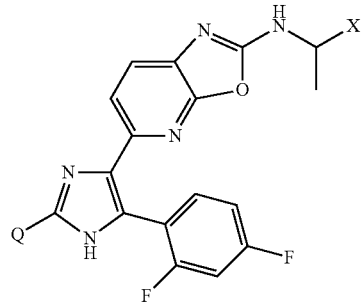

where:

X is methoxyethyl or ethoxymethyl;

Q is cyclopropyl, 2-methyl-propanol-2-yl, 3-methyloxetan-3-yl, 1-hydroxymethyl-1-cyclopropyl;

or a pharmaceutically acceptable salt thereof;

wherein the cancer is selected from ovarian cancer and multiple myeloma.

10. The method of claim 9 wherein the cancer is ovarian cancer.

11. The method of claim 9 wherein the cancer is multiple myeloma.

12. A method of treating renal cancer comprising administering to a mammal in need of such treatment an effective amount of a compound of the formula:

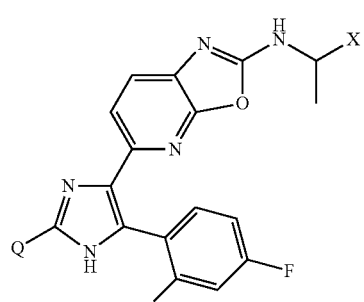

where:

X is methoxyethyl or ethoxymethyl;

Q is cyclopropyl, 2-methyl-propanol-2-yl, 3-methyloxetan-3-yl, 1-hydroxymethyl-1-cyclopropyl;

or a pharmaceutically acceptable salt thereof;

in combination with sunitinib.

13. The method of claim 12 wherein the compound or salt is administered in simultaneous, separate or sequential combination with sunitinib.

* * * * *

UNITED STATES PATENT AND TRADEMARK OFFICE
CERTIFICATE OF CORRECTION

PATENT NO. : 8,288,548 B2
APPLICATION NO. : 13/298319
DATED : October 16, 2012
INVENTOR(S) : David Andrew Coates et al.

It is certified that error appears in the above-identified patent and that said Letters Patent is hereby corrected as shown below:

On the Title page, Item (54) and in Column 1, Line 1, Title, Delete "[5-4-b]" and insert -- [5,4-B] --, Column 43, Line 22, In Claim 2, delete "difluorophenyl -4" and insert -- difluorophenyl)-4 --, Column 43, Line 42, In Claim 5, delete "methyl -propyl]" and insert -- methyl-propyl] --, Column 43, Line 45 (Approx.), In Claim 6, delete "difluorophenyl) -2" and insert -- difluorophenyl)-2 --, Column 43, Line 47 (Approx.), In Claim 6, delete "salt." and insert -- salt thereof. --, Column 43, Line 51 (Approx.), In Claim 7, delete "salt." and insert -- salt thereof. --, Signed and Sealed this
Fourth Day of December, 2012

David J. Kappos
*Director of the United States Patent and Trademark Office*